United States Patent
Fevola et al.

(10) Patent No.: US 9,937,118 B2
(45) Date of Patent: Apr. 10, 2018

(54) CLEAR SUSPENDING PERSONAL CARE CLEANSING COMPOSITIONS

(71) Applicant: Johnson & Johnson Consumer Inc., Skillman, NJ (US)

(72) Inventors: Michael J. Fevola, Belle Mead, NJ (US); Tobias J. Fuetterer, Princeton, NJ (US); Jeffrey D. Martin, Hillsborough, NJ (US); Snehal M. Shah, Hillsborough, NJ (US); Aliaksandr Zhuk, Warrington, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/278,175

(22) Filed: Sep. 28, 2016

(65) Prior Publication Data
US 2017/0360680 A1 Dec. 21, 2017

Related U.S. Application Data

(60) Provisional application No. 62/352,615, filed on Jun. 21, 2016.

(51) Int. Cl.
| | |
|---|---|
| *C11D 1/02* | (2006.01) |
| *C11D 1/88* | (2006.01) |
| *C11D 3/20* | (2006.01) |
| *C11D 3/37* | (2006.01) |
| *A61K 8/06* | (2006.01) |
| *A61K 8/81* | (2006.01) |
| *A61Q 19/10* | (2006.01) |
| *A61K 8/365* | (2006.01) |
| *A61K 8/368* | (2006.01) |
| *A61K 8/44* | (2006.01) |
| *A61K 8/46* | (2006.01) |
| *A61K 8/73* | (2006.01) |

(52) U.S. Cl.
CPC .............. *A61K 8/8147* (2013.01); *A61K 8/06* (2013.01); *A61K 8/365* (2013.01); *A61K 8/368* (2013.01); *A61K 8/44* (2013.01); *A61K 8/466* (2013.01); *A61K 8/732* (2013.01); *A61K 8/8152* (2013.01); *A61K 8/8158* (2013.01); *A61Q 19/10* (2013.01); *A61K 2800/262* (2013.01); *A61K 2800/546* (2013.01); *A61K 2800/5424* (2013.01); *A61K 2800/5428* (2013.01); *A61K 2800/594* (2013.01)

(58) Field of Classification Search
CPC .... C11D 1/02; C11D 1/88; C11D 3/20; C11D 3/37; C11D 3/3746; C11D 3/3796; A61K 8/06; A61K 8/81; A61Q 19/10
See application file for complete search history.

(56) References Cited

U.S. PATENT DOCUMENTS

| | | | |
|---|---|---|---|
| 3,035,004 | A | 5/1962 | Glavis |
| 4,110,263 | A | 8/1978 | Lindemann et al. |
| 4,186,113 | A | 1/1980 | Verdicchio et al. |
| 4,410,673 | A | 10/1983 | Schulz et al. |
| 4,443,362 | A | 4/1984 | Guth et al. |
| 4,628,071 | A | 12/1986 | Morgan |
| 4,726,915 | A | 2/1988 | Verdicchio |
| 5,292,843 | A | 3/1994 | Jenkins et al. |
| 5,326,843 | A | 7/1994 | Lorah et al. |
| 5,876,705 | A | 3/1999 | Uchiyama et al. |
| 6,140,435 | A | 10/2000 | Zanotti Russo |
| 6,897,253 | B2 | 5/2005 | Schmucker Castner et al. |
| 7,288,616 | B2 | 10/2007 | Tamareselvy et al. |
| 7,335,627 | B1 | 2/2008 | O'Lenick et al. |
| 7,375,064 | B1 | 5/2008 | O'Lenick, Jr. |
| 7,417,020 | B2 | 8/2008 | Fevola et al. |
| 7,507,399 | B1 | 3/2009 | O'Lenick, Jr. |
| 8,258,250 | B2 | 9/2012 | Fevola et al. |
| 8,329,627 | B2 | 12/2012 | Gunn et al. |
| 8,399,590 | B2 | 3/2013 | Gardner et al. |
| 9,187,590 | B2 | 11/2015 | Tamareselvy et al. |
| 2006/0270563 | A1 | 11/2006 | Yang et al. |
| 2011/0081309 | A1 | 4/2011 | Fevola et al. |
| 2013/0115185 | A1 | 5/2013 | Tamareselvy et al. |
| 2013/0189198 | A1 | 7/2013 | Tamareselvy |
| 2016/0106647 | A1 | 4/2016 | Fevola et al. |

FOREIGN PATENT DOCUMENTS

| | | | | |
|---|---|---|---|---|
| DE | 102012222979 | * | 6/2014 | ............... A61K 8/04 |
| WO | WO 2009/016375 A | | 2/2009 | |
| WO | WO 2012/006402 | * | 1/2012 | ............ C08F 265/06 |

OTHER PUBLICATIONS

Jenkins et al., "Glossary of Basic Terms in Polymer Science", Pure Appl. Chem. (1996) 68:2287-2311.

(Continued)

*Primary Examiner* — Brian P Mruk

(57) ABSTRACT

Compositions of the present invention include an anionic surfactant, a zwitterionic surfactant, a superhydrophilic amphiphilic copolymer, an organic acid; and a polymer selected from the group consisting of a non-hydrophobically modified alkali-swellable emulsion polymer and a non-crosslinked hydrophobically modified acid-swellable emulsion polymer, wherein, when the composition contains the non-hydrophobically modified alkali-swellable emulsion polymer, the non-hydrophobically modified alkali-swellable emulsion polymer is present in an amount of about 0.1% to 5% by weight, and when the composition contains the non-crosslinked hydrophobically modified acid-swellable emulsion polymer, the non-hydrophobically modified acid-swellable emulsion polymer is present in an amount of about 0.1% to 5% by weight, and wherein the composition has an NTU value of 95 or less, a yield value of about 0.1 Pascal or more and pH of from about 3 to about 6.5.

10 Claims, No Drawings

(56) References Cited

OTHER PUBLICATIONS

European search report and opinion dated Sep. 8, 2017, for EP 17177233.8.
Mintel Database [Online], "Shampoo", Jul. 1, 2015, Database accession No. 3343745 (XP002773189).

* cited by examiner

CLEAR SUSPENDING PERSONAL CARE CLEANSING COMPOSITIONS

This application claims the benefit of U.S. Provisional Application 62/352,615 filed Jun. 21, 2016, the complete disclosure of which is hereby incorporated herein by reference for all purposes.

FIELD OF THE INVENTION

The present invention relates to clear personal care cleansing compositions containing polymeric benefiting ingredients with the ability to suspend.

BACKGROUND OF THE INVENTION

Cleansing compositions for use on or near skin and/or eyes have to fulfill many different requirements. Typically, good cleansing properties and high foam volume require higher levels of detergents, which tend to be irritating to skin and/or eyes. Hence, it is desirable to reduce the concentration of detergent used in a composition, while maintaining good cleansing and foaming properties. For certain compositions it is desirable to combine the ability to suspend insoluble components, such as scrubbing beads or gas bubbles, while having good clarity of the liquid phase of the composition, such that the suspended components can be easily seen throughout the composition. For certain compositions it is desirable to have an acidic pH instead of a neutral or more basic pH to e.g. allow utilization of organic acid derivatives as preservatives or benefit agents, such as benzoic acid as an effective preservative or salicylic acid as an anti-acne agent.

While there are certain attempts to address the above requirements individually, it is desirable to generate cleansing compositions exhibiting a yield stress value sufficient to suspend insoluble components, and having a good clarity, and having a pH below neutral (acidic), and maintaining mildness to skin and/or eyes while having good cleansing and foaming properties. Typically, rheology modifiers providing a yield stress value to a composition render the composition turbid, especially in presence of only a medium or low concentration of surfactant. Some rheology modifier polymers providing a yield stress value can generate clear compositions at a pH above 6.5, but will render the composition turbid at acidic pH, again in presence of a medium to low concentration of surfactant. Acrylates Copolymer like Carbopol® Aqua SF-1 is an example of the latter. Certain attempts to produce clear suspending compositions at a pH below 6.5 using polymers like Acrylates Copolymer as a suspending polymer have included utilization of high amounts of anionic surfactant in the composition. A high concentration of surfactant can improve clarity, but render the composition irritating to skin and eyes and thus, is undesirable. Certain attempts to produce clear suspending compositions at a pH below 6.5 have included the use of acid swellable suspending polymers, e.g. a Polyacrylate-1 Crosspolymer like Carbopol® Aqua CC. However, also these polymers require high amounts of anionic surfactant to generate clear compositions and thus, are undesirable. The polysaccharide derived rheology polymer xanthan gum can generate suspending compositions at a pH below 6.5, but this polymer becomes less efficient at a pH below 6.5 compared with neutral and basic pH and more importantly, it is generating an undesirable texture and thus makes the composition undesirable for Personal Care use.

Certain attempts to produce milder cleansing compositions have included combining relatively low amounts of anionic surfactants, with relatively lower irritating surfactants such as nonionic and/or amphoteric surfactants, see, e.g. U.S. Pat. No. 4,726,915, or associating the anionic surfactants with amphoteric or cationic compounds in order to yield surfactant complexes, see, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance, and will not generate clear compositions when combined with suspending polymers such as Acrylates Copolymer (e.g. Carbopol® Aqua SF-1) or Polyacrylate-1 Crosspolymer (e.g. Carbopol® Aqua CC) at a pH below 6.5. Still another approach to producing mild cleansing compositions is to use polymerized surfactants having a relatively low degree-of-polymerization and at least about 10 mol % amphiphilic repeat units; see e.g. U.S. Pat. No. 7,417,020. Still another approach to producing mild cleansing compositions is to use super hydrophilic amphiphilic copolymers; see e.g. U.S. Pat. No. 8,258,250 B2. While they teach how to generate mild cleansing compositions, both the latter and the former approach do not teach how to generate mild and clear and suspending compositions at a pH of below 6.5.

Thus, while improvements have been made in providing solutions for the individual requirements or the combination of some of the requirements of cleansing compositions, the inventors have recognized that it is desirable to generate compositions fulfilling several requirements simultaneously: mildness to the skin and eyes, while maintaining good cleansing and foaming properties, the ability to suspend insoluble components, while having good clarity of the liquid phase of the composition, and having an acidic pH instead of a neutral or more basic pH to e.g., allow utilization of organic acid derivatives.

SUMMARY OF THE INVENTION

The present invention provides compositions containing an anionic surfactant, a zwitterionic surfactant, a superhydrophilic amphiphilic copolymer, an organic acid and a polymer selected from the group consisting of a non-hydrophobically modified alkali-swellable emulsion polymer and a non-crosslinked hydrophobically modified acid-swellable emulsion polymer, wherein, when the composition contains the non-hydrophobically modified alkali-swellable emulsion polymer, the non-hydrophobically modified alkali-swellable emulsion polymer is present in an amount of about 0.1% to 5% by weight, and when the composition comprises the non-crosslinked hydrophobically modified acid-swellable emulsion polymer, the non-hydrophobically modified acid-swellable emulsion polymer is present in an amount of about 0.1% to 5% by weight, and wherein the composition has an NTU value of 95 or less, a yield value of about 0.1 Pascal or more and pH of from about 3 to about 6.5.

DETAILED DESCRIPTION OF THE INVENTION

Applicants have discovered that compositions of the present invention overcome the disadvantages of the prior art and provide compositions that exhibit desirable clarity and are mild to the skin and eyes, as compared to the prior art, while having the ability to suspend (i.e. exhibit a yield value) and maintain foaming and viscosity properties desirable for a cleansing composition. The compositions of the present invention comprise of an anionic surfactant, a zwitterionic surfactant, a superhydrophilic amphiphilic copolymer (SAC), an organic acid and a polymer selected from the group consisting of a non-hydrophobically modified alkali-swellable emulsion (nASE) polymer and a non-crosslinked hydrophobically modified acid-swellable emulsion (HacidSE) polymer.

The composition may further comprise ingredients selected from the group consisting of surfactants other than the zwitterionic or anionic surfactants, e.g. nonionic and/or cationic surfactants, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, inorganic salts, solvents, viscosity controlling agents and opacifying agents.

For example, as shown in the Examples, compositions of the present invention comprising a nASE polymer, a SAC, an anionic surfactant, a zwitterionic surfactant and an organic acid exhibit an NTU value of 95 or less, a yield value of about 0.1 Pascal or more and are mild to the skin and eyes as well, whereas compositions containing a rheology polymer other than a nASE polymer or a non-crosslinked HacidSE polymer are not clear and/or are not mild, as shown in the Comparative Examples.

Where applicable, chemicals are specified according to their INCI Name. Additional information, including suppliers and trade names, can be found under the appropriate INCI monograph in the *International Cosmetic Ingredient Dictionary and Handbook*, 15$^{th}$ *Edition* published by the Personal Care Products Council, Washington D.C.

All percentages listed in this specification are percentages by weight, unless otherwise specifically mentioned. Percentages and weights of components like polymer, surfactant, salt, acids, etc., listed in this specification are percentages and weights of active of a component excluding, e.g., solvents like the water of an aqueous sodium chloride solution added to a composition.

As used herein, "wt %" refers to weight percent, i.e. % weight/weight; e.g. 5 g Sodium Chloride in 95 g water is 5 wt % active Sodium Chloride in aqueous solution.

"Non hydrophobically modified" as used herein, means that the polymer has no or only minor amounts of monomers containing a hydrophobic side group (a hydrophobic monomer, or also referred to as associative monomer). Typically, the amount of monomer(s) containing a hydrophobic side group is about 1 wt % or lower, more typically about 0.5 wt % or lower, and even more typically about 0.1 wt % or lower. Exceptions are crosslinker monomers/molecules, which may have side chains with greater than 4 carbon atoms, but are not considered a hydrophobic monomer (and their use level in the polymer is typically low, i.e. less than 1 wt %).

"Hydrophobically modified", as used herein, means that the polymer contains a hydrophobicmonomer, i.e. a monomer bearing a hydrophobic side group, in amounts greater than 0% by weight, or greater than 0.1% by weight, or greater than 1.0% by weight, or greater than 10% by weight.

"Hydrophobic side group", as used herein, means a hydrophobic moiety that contains at least one of the following: (a) a carbon-carbon chain of at least five carbons in which none of the five carbons is a carbonyl carbon or has a hydrophilic moiety bonded directly to it; (b) two or more alkyl siloxy groups (—[Si(R)$_2$—O]—); and/or (c) two or more oxypropylene groups in sequence. A hydrophobic moiety may be, or include, linear, cyclic, aromatic, saturated or unsaturated groups. In certain preferred embodiments, hydrophobic moieties comprise a carbon chain of at least six or more carbons, more preferably seven or more carbons, in which none of the carbons in such chain have a hydrophilic moiety bonded directly thereto. Certain other preferred hydrophobic moieties include moieties comprising a carbon chain of about eight or more carbon atoms, more preferably about 10 or more carbon atoms in which none of the carbons in such chain have a hydrophilic moiety bonded directly thereto. Examples of hydrophobic functional moieties may include esters, ketones, amides, carbonates, urethanes, carbamates, or xanthate functionalities, and the like, having incorporated therein or attached thereto a carbon chain of at least four carbons in which none of the four carbons has a hydrophilic moiety bonded directly to it. Other examples of hydrophobic moieties include groups such as poly(oxypropylene), poly(oxybutylene), poly(dimethylsiloxane), fluorinated hydrocarbon groups containing a carbon chain of at least four carbons in which none of the four carbons has a hydrophilic moiety bonded directly to it, and the like.

Hydrophobic monomers (also referred to as "associative" monomers) used in hydrophobically modified polyelectrolytes are described for example in U.S. Pat. Nos. 5,292,843, 6,897,253, 7,288,616, 3,035,004, and U.S. Patent Publication No. 2006/0270563, the contents each of which is hereby incorporated by reference in their entirety.

As used herein, the term "hydrophilic moiety" is any anionic, cationic, zwitterionic, or nonionic group that is polar. Nonlimiting examples include anionics such as: sulfate, sulfonate, carboxylic acid/carboxylate, phosphate, phosphonates, and the like; cationics such as: amino, ammonium, including mono-, di-, and trialkylammonium species, pyridinium, imidazolinium, amidinium, poly(ethyleneiminium), and the like; zwitterionics such as: ammonioalkylsulfonate, ammonioalkylcarboxylate, amphoacetate, and the like; and nonionics: such as hydroxyl, sulfonyl, ethyleneoxy, amido, ureido, amine oxide, and the like.

Specific Examples of hydrophobic monomers include, but are not limited to:

Acrylic hydrophobic monomer according to structure (1):

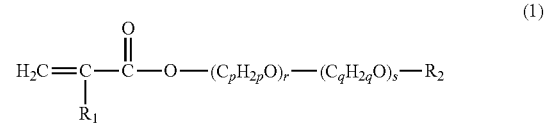

wherein
R$_2$ is linear or branched or cyclic (C$_5$-C$_{50}$) alkyl, hydroxyalkyl, alkoxyalkyl, aryl, or aralkyl,
R$_1$ is H, or methyl, or ethyl, and
p and q are each independently of each other 2, or 3, or 4
r and s are each independently of each other 0-50
t is 1-50.

In one embodiment, the hydrophobic monomer is a compound according to structure 1, wherein R$_2$ is linear (C$_{16}$-C$_{22}$) alkyl. In one embodiment, the hydrophobic monomer is a compound according to structure 1, wherein R$_2$ is a (C$_5$-C$_{50}$) alkyl group. In one embodiment, the hydrophobic monomer is a compound according to structure 1, wherein p=0 and s=0 and R$_2$ is a (C$_5$-C$_{50}$) alkyl group. In one embodiment, the hydrophobic monomer is a compound according to structure 1, wherein p=2, s=0, and t=1. In one embodiment, the hydrophobic monomer is a compound according to structure 1, wherein $R_2$ is linear ($C_{16}$-$C_{22}$) alkyl, $R_1$ is H or methyl, p=0-2, s=0, and t=1.

Suitable ethylenically unsaturated hydrophobic monomers include:

- alkyl-(meth)acrylates that comprise at least one linear or branched ($C_5$-$C_{40}$) alkyl-group per molecule, such as pentyl-(meth)acrylates, hexyl-(meth)acrylates, tridecyl-(meth)acrylates, myristyl-(meth)acrylates, cetyl-(meth)acrylates, stearyl-(methyl)acrylates, behenyl polyalkoxylated (meth)acrylates, and mixtures thereof,
- alkyl-polyether (meth)acrylates that comprise at least one linear or branched ($C_5$-$C_{40}$) alkyl-polyether group per molecule, such as hexyl polyalkoxylated (meth)acrylates, tridecyl polyalkoxylated (meth)acrylates, myristyl polyalkoxylated (meth)acrylates, cetyl polyalkoxylated (meth)acrylates, stearyl polyalkoxylated (methyl) acrylates, eicosyl polyalkoxylated (meth)acrylates, behenyl polyalkoxylated (meth)acrylates, melissyl polyalkoxylated (meth)acrylates, tristyrylphenoxyl polyalkoxylated (meth)acrylates, and mixtures thereof,
- alkyl-polyether (meth)acrylamides that comprise at least one ($C_5$-$C_{40}$) alkyl-polyether substituent group per molecule, such as hexyl polyalkoxylated (meth)acrylamides, tridecyl polyalkoxylated (meth)acrylamides, myristyl polyalkoxylated (meth)acrylamides, cetyl polyalkoxylated (meth)acrylamides, stearyl polyalkoxylated (methyl)acrylamides, eicosyl polyalkoxylated (meth)acrylamides, behenyl polyalkoxylated (meth)acrylamides, melissyl polyalkoxylated (meth) acrylamides and mixtures thereof,
- alkyl-polyether vinyl esters, alkyl-polyether vinyl ethers, or alkyl-polyether vinyl amides that comprise at least one ($C_5$-$C_{40}$) alkyl-polyether substituent group per molecule such as vinyl stearate polyalkoxylate, myristyl polyalkoxylated vinyl ether, and mixtures thereof,
- as well as mixtures of two or more of any of the above alkyl-polyether acrylates, alkyl-polyether methacrylates, alkyl-polyether acrylamides, alkyl-polyether methacrylamides, alkyl-polyether vinyl esters, alkyl-polyether vinyl ethers, and alkyl-polyether vinyl amides.
- cyclohexyl(meth)acrylate, 2-ethylhexyl (meth)acrylate, isodecyl(meth)acrylate, lauryl(meth)acrylate isobornyl (meth)acrylate, benzyl(meth)acrylate, phenoxyethyl (meth)acrylate, tetrahydrofurfuryl(meth)acrylate, glycidyl(meth)acrylate, vinyl 2-ethylhexanoate, and N-tert-octyl(meth)acrylamide.
- In one embodiment, the hydrophobic monomer comprises one or more alkyl-polyalkoxylated (meth)acrylates that comprise one linear or branched ($C_5$-$C_{40}$) alkyl-polyethoxylated group, more typically ($C_{10}$-$C_{22}$) alkyl-polyethoxylated group per molecule, such as decyl-polyethoxylated (meth)acrylates, tridecyl-polyethoxylated (meth)acrylates, myristyl-polyethoxylated (meth)acrylates, cetyl-polyethoxylated (meth)acrylates, stearyl-polyethoxylated (methyl)acrylates, eicosyl-polyethoxylated (meth)acrylates, behenyl-polyethoxylated (meth)acrylates, even more typically decyl-polyethoxylated methacrylates, tridecyl-polyethoxylated methacrylates, myristyl-polyethoxylated methacrylates, cetyl-polyethoxylated methacrylates, stearyl-polyethoxylated methylacrylates, eicosyl-polyethoxylated methacrylates, behenyl-polyethoxylated methacrylates, and mixtures thereof.

nASE Polymer Chemistry

As used herein, the term "non-hydrophobically modified alkali-swellable emulsion polymer", or "nASE polymer", refers to a non-hydrophobically modified alkali swellable emulsion polymer (nASE), wherein the nASE polymer may optionally contain a crosslinker, and/or may optionally be a crosslinked polymer. Compositions of the present invention may contain from about 0.1% to about 5% by weight, more preferably from about 0.5% to about 2.5% by weight, and even more preferable from about 0.75% to about 2% by weight, of the nASE polymer, when used in such compositions.

In certain embodiments, the nASE polymer may be a (co)polymer made from ethylenically unsaturated monomers, e.g., an acrylate or vinyl (co)polymer. In one embodiment the nASE polymer may be an acrylates (co)polymer comprising one or more monomers selected from the group consisting of (meth)acrylic acid, simple alkyl-esters of (meth)acrylic acid, (including methyl-, ethyl-, propyl-, butyl-ester), simple hydroxyalkyl-esters (including hydroxyethyl-ester, hydroxybutyl-ester) and simple alkoxyalkyl-esters (including methoxyethyl-ester, ethoxyethyl-ester). "Simple" alkyl-ester refers to the alkyl-group having from 1 to 4 carbons. The amount of simple alkyl-ester (meth)acrylate monomer in the polymer may range from about 5% to about 80% by weight, or from about 10% to about 70% by weight, or about 30% to about 70% by weight, or from about 30% to about 60% by weight. Specific examples of simple alkyl-ester (meth)acrylate monomers include methyl(meth)acrylate, ethyl(meth)acrylate, butyl (meth)acrylate, isobutyl(meth)acrylate, (meth) hydroxyethyl (meth)acrylate, hydroxypropyl(meth)acrylate, methoxyethyl (meth)acrylate, and ethoxyethyl acrylate.

In certain embodiments the nASE polymer further comprises at least one monomer comprising at least one acid moiety exhibiting a pKa value lower than that of methacrylic acid. The amount of monomer containing at least one acid moiety exhibiting a pKa value lower than that of methacrylic acid in the polymer ranges from about 0.5% to about 80% by weight, or from about 0.5% to about 60% by weight, or about 1% to about 40% by weight, or about 1% to about 20% by weight, or about 1% to about 10% by weight.

Examples of such monomers include, ethylenically unsaturated dicarboxylic acid monomers, such as maleic acid, itaconic acid and fumaric acid, as well as ethylenically unsaturated sulphonic acid monomers, such as vinyl sulfonic acid, 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups.

In certain embodiments, the acid moiety is a sulfonate group such as 2-acrylamido-2-methylpropane sulfonic acid (AMPS) and its salts. In other embodiments, the acid moiety is a carboxylic group such as acrylic acid (AA) and its salts. In yet other embodiments, the monomer comprising the acid moiety is itaconic acid and its salts.

The nASE polymer can contain other monomers, for example, ethylenically unsaturated monomers such as acrylamide, dimethyl-acrylamide, and diacetone (meth)acrylamide, vinyl esters such as vinyl acetate, vinyl propionate, N-vinylamides such as: N-vinylpyrrolidione, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene, acetoxyethyl (meth)acrylate, (meth)acrylamides such as, (meth)acrylamide, N-methylol (meth)acrylamide, N-butoxyethyl(meth)acrylamide, N,N-dimethyl (meth)acrylamide, N-isopropyl(meth)acrylamide, N-tert-butyl (meth)acrylamide, and ethylenically unsaturated alkyl esters of dicarboxylic acid monomers, such as butyl methyl maleate, dimethylaminoethyl(meth)acrylate, diethylaminoethyl (meth)acrylate, tert-butylaminoethyl(meth)acrylate.

Crosslinking (XL) Monomers:

The nASE polymers utilized in compositions of the present invention can be prepared from a monomer mixture comprising one or more crosslinking monomers for introducing branching and controlling molecular weight. Suitable polyunsaturated crosslinkers are well known in the art. Mono-unsaturated compounds carrying a reactive group that is capable of causing a formed copolymer to be crosslinked before, during, or after polymerization has taken place can also be utilized. Other useful crosslinking monomers include polyfunctional monomers containing multiple reactive groups such as epoxide groups, isocyanate groups, and hydrolyzable silane groups. Various polyunsaturated compounds can be utilized to generate either a partially or substantially cross-linked three dimensional network.

Examples of suitable polyunsaturated crosslinking monomer components include, but are not limited to, polyunsaturated aromatic monomers such as divinylbenzene, divinyl naphthylene, and trivinylbenzene; polyunsaturated alicyclic monomers, such as 1,2,4-trivinylcyclohexane; di-functional esters of phthalic acid such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers include, but are not limited to, polyalkenyl ethers such as triallyl pentaerythritol, diallyl pentaerythritol, diallyl sucrose, octaallyl sucrose, and trimethylolpropane diallyl ether; polyunsaturated esters of polyalcohols or polyacids such as 1,6-hexanediol di(meth)acrylate, tetramethylene tri (meth)acrylate, allyl(meth)acrylate, diallyl itaconate, diallyl fumarate, diallyl maleate, trimethylolpropane tri(meth)acrylate, trimethylolpropane di(meth)acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, and triethyleneglycol di(meth)acrylate; polyunsaturated silanes, such as dimethyldivinylsilane, methyltrivinylsilane, allyldimethylvinylsilane, diallyldimethylsilane, and tetravinylsilane; polyunsaturated stannanes, such as tetraallyl tin, and diallyldimethyl tin; and the like.

Useful monounsaturated compounds carrying a reactive group include N-methylolacrylamide; N-alkoxy(meth)acrylamide, wherein the alkoxy group is a $C_1$ to $C_{18}$ alkoxy; and unsaturated hydrolyzable silanes such as triethoxyvinylsilane, tris-isopropoxyvinylsilane, and 3-triethoxysilylpropyl methacrylate; and the like.

Useful polyfunctional crosslinking monomers containing multiple reactive groups include, but are not limited to, hydrolyzable silanes such as ethyltriethoxysilane and ethyltrimethoxysilane; epoxy-substituted hydrolyzable silanes, such as 2-(3,4-epoxycyclohexyl)ethyltriethoxysilane and 3-glycidoxypropyltrimethoxysilane; polyisocyanates, such as 1,4-diisocyanatobutane, 1,6-diisocyanatohexane, 1,4-phenylenediisocyanate, and 4,4'-oxybis(phenylisocyanate); unsaturated epoxides, such as glycidyl methacrylate and alkylglycidyl ether; polyepoxides, such as diglycidyl ether, 1,2,5,6-diepoxyhexane, and ethyleneglcoldiglycidyl ether; and the like.

Also useful are polyunsaturated crosslinkers derived from ethoxylated polyols, such as diols, triols and bis-phenols, ethoxylated with about 2 to about 100 moles of ethylene oxide per mole of hydroxyl functional group and end-capped with a polymerizable unsaturated group such as a vinyl ether, allyl ether, acrylate ester, methacrylate ester, and the like. Examples of such crosslinkers include bisphenol A ethoxylated dimethacrylate; bisphenol F ethoxylated dimethacrylate, ethoxylated trimethylol propane trimethacrylate, and the like. Other ethoxylated crosslinkers useful in the multi-purpose polymers of the present invention include ethoxylated polyol-derived crosslinkers disclosed in U.S. Pat. No. 6,140,435, the relevant disclosure of which is incorporated herein by reference.

Examples of particularly suitable XL monomers include, but are not limited to, acrylate and methacrylate esters of polyols having at least two acrylate or methacrylate ester groups, such as trimethylolpropane triacrylate (TMPTA), ethoxylated-3 trimethylolpropane triacrylate (TMPEO3TA), ethoxylated-15 trimethylolpropane triacrylate (TMPEO15TA), trimethylolpropane dimethacrylate, triethylene glycol dimethacrylate (TEGDMA), ethoxylated (30) bisphenol A dimethacrylate (EOBDMA); polyalkenyl ethers (APE) such as triallyl pentaerythritol, diallyl pentaerythritol, and trimethylolpropane diallyl ether (TMPDAE); sucrose allyl ethers (AS) such as diallyl sucrose, octaallyl sucrose; alkylene bisacrylamides, such as methylene bisacrylamide (MBA), propylene bisacrylamide; and suitable mixtures of any two or more thereof.

When utilized, crosslinking monomers are present in the monomer reaction mixture in an amount of up to about 5 weight percent, based on total monomer mixture weight. In another embodiment, the XL monomers are present in an amount of about 0.01 weight percent to about 5 weight percent, or from about 0.05 weight percent to about 4 weight percent, or from about 0.1 weight percent to about 2 weight percent, or even from about 0.5 weight percent to about 1 weight percent of the monomer mixture based on the total monomer mixture weight. Preferred examples for the nASE polymer include Acrylates Copolymer and/or Acrylates Crosspolymer-4. Methods of making nASE polymers are described in U.S. Pat. Nos. 5,326,843, 4,628,071, and 4,410,673, the contents each of which are incorporated herein by reference in their entirety.

Non-Crosslinked Hydrophobically-Modified Acid-Swellable Emulsion Chemistry

Compositions of the present invention may contain from about 0.1% to 5% by weight of a non-crosslinked hydrophobically modified acid-swellable emulsion (HacidSE) polymer, or "non-crosslinked HacidSE polymer", more preferably from about 0.5% to about 2.5% by weight, and even more preferable from about 0.75% to about 2% by weight.

"Non-crosslinked polymer", as used herein, means a polymer that is substantially free of covalent bond linkages between polymer chains. The HacidSE polymer may be a (co)polymer made from ethylenically unsaturated monomers, e.g., an acrylate or vinyl (co)polymer. The HacidSE polymer may be an acrylates copolymer consisting of a) one or more monomers of (meth)acrylic acid and/or one of their simple alkyl-esters (including methyl-, ethyl-, propyl-, butyl-ester) and simple hydroxyalkyl-esters (including hydroxyethyl-ester, hydroxybutyl-ester) and simple alkoxyalkyl-esters (including methoxyethyl-ester, ethoxyethyl-ester) and b) at least one monomer containing a hydrophobic side group containing more than 4 carbon atoms (the hydrophobic monomer) and c) an acid soluble/swellable monomer. In certain embodiments the HacidSE polymer may contain at least one monomer of the group of $C_{1-4}$ alkylamino(meth)acrylate (ASMA) or $C_{1-4}$ alkylamino(meth)acrylamide as the acid soluble/swellable monomer.

ASMA Monomer:

Amino-substituted meth(acrylate) (ASMA) monomers suitable for the preparation of the HacidSE polymers are basic, polymerizable, ethylenically unsaturated monomers that contain at least one amino functional group. These basic amino groups can be derived from mono-, di- or poly-amino alkyl groups or nitrogen containing heteroaromatic groups. The amino group can comprise primary, secondary or tertiary amines. The monomers can be used in the amino form or in the salt form, as desired.

The HacidSE polymers utilized in compositions of the present invention include, in one embodiment, one or more ASMA monomers selected from the monomers represented by structures (2) and (3) shown below:

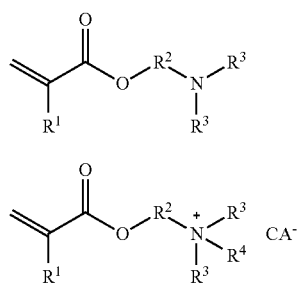

where $R^1$ is methyl; where $R^2$ is a substituted or unsubstituted, linear or branched $C_2$ to $C_8$ alkanediyl group (i.e., an alkane group having at least two free valencies), with the proviso that when $R^2$ has two carbons at least one of the two carbon atoms of the $R^2$ group is substituted (e.g., monosubstituted or di-substituted) with a linear or branched $C_1$ to $C_{30}$ alkyl group; where each $R^3$ is independently selected from hydrogen, linear or branched $C_1$ to $C_{30}$ alkyl groups, linear or branched $C_1$ to $C_{30}$ alkyl groups that contain one or more heteroatoms, linear or branched $C_2$ to $C_{20}$ alkenyl groups, linear or branched $C_2$ to $C_{30}$ alkenyl groups that contain one or more heteroatoms, linear or branched $C_2$ to $C_{30}$ alkynyl groups, linear or branched $C_2$ to $C_{30}$ alkynyl groups that contain one or more heteroatoms, $C_4$ to $C_{20}$ aryl groups, $C_4$ to $C_{20}$ aryl groups that contain one or more heteroatoms, $C_4$ to $C_{20}$ cycloalkyl groups, $C_4$ to $C_{20}$ cycloalkyl groups that contain one or more heteroatoms, $C_4$ to $C_{20}$ heterocyclic groups, or where both $R_3$ substituents and the nitrogen atom to which they are attached can form a saturated or unsaturated $C_2$ to $C_{20}$ heterocyclic group or a saturated or unsaturated $C_2$ to $C_{20}$ heterocyclic group having two or more heteroatoms, where the heteroatoms, if present, are selected from a carbonyl group, N, S, P or O; $R^4$ is a linear or branched $C_1$ to $C_{30}$ alkyl group; and where CA– is a counter-anion suitable to balance the charge on the quaternary ammonium moiety. In another embodiment, $R^1$ is methyl; where $R^2$ is a substituted or unsubstituted, linear or branched $C_3$ to $C_7$ alkanediyl group (i.e., an alkane group having at least two free valencies); where each $R^3$ is independently selected from hydrogen, linear or branched $C_3$ to $C_{15}$ alkyl groups, linear or branched $C_3$ to $C_{15}$ alkyl groups that contain one or more heteroatoms, linear or branched $C_4$ to $C_{20}$ alkenyl groups, linear or branched $C_4$ to $C_{20}$ alkenyl groups that contain one or more heteroatoms, linear or branched $C_4$ to $C_{20}$ alkynyl groups, linear or branched $C_4$ to $C_{20}$ alkynyl groups that contain one or more heteroatoms, $C_5$ to $C_{10}$ aryl groups, $C_5$ to $C_{10}$ aryl groups that contain one or more heteroatoms, $C_5$ to $C_{10}$ cycloalkyl groups, $C_5$ to $C_{10}$ cycloalkyl groups that contain one or more heteroatoms, $C_5$ to $C_{10}$ heterocyclic groups, or where both $R^3$ substituents and the nitrogen atom to which they are attached can form a saturated or unsaturated $C_3$ to $C_{10}$ heterocyclic group or a saturated or unsaturated $C_3$ to $C_{10}$ heterocyclic group having two or more heteroatoms, where the heteroatoms, if present, are selected from a carbonyl group, N, S, P or O; $R^4$ is a linear or branched $C_2$ to $C_{20}$ alkyl group; and where CA– is a counter-anion suitable to balance the charge on the quaternary ammonium moiety. Here, as well as elsewhere in the specification and claims, individual numerical values (including carbon atom numerical values), or limits, can be combined to form additional non-disclosed and/or non-stated ranges.

The HacidSE polymer can contain other monomers. Examples for other monomers include, e.g., acrylamide, dimethyl-acrylamide, and diacetone (meth)acrylamide, vinyl esters such as vinyl acetate, vinyl propionate, N-vinylamides, such as: N-vinylpyrrolidone, N-vinylcaprolactam, N-vinylformamide, and N-vinylacetamide, and vinyl ethers, such as: methyl vinyl ether, ethyl vinyl ether, butyl vinyl ether, and hydroxybutyl vinyl ether, and ethylenically unsaturated aryl compounds, such as: styrene, acetoxyethyl (meth)acrylate; (meth)acrylamides, such as: (meth)acrylamide, N-methylol (meth)acrylamide, N-butoxyethyl(meth)acrylamide, N,N-dimethyl (meth)acrylamide, N-isopropyl(meth)acrylamide, and N-tert-butyl (meth)acrylamide, and ethylenically unsaturated alkyl esters of dicarboxylic acid monomers, such as: butyl methyl maleate, dimethylaminoethyl(meth)acrylate, diethylaminoethyl(meth)acrylate, and tert-butylaminoethyl(meth)acrylate.

Examples of HacidSE polymers include: Acrylates/Aminoacrylates/$C_{10-30}$ Alkyl PEG-20 Itaconate Copolymers.

Compositions of the present invention exhibit a yield value. As used herein, the term "yield value" means that the elastic modulus of the compositions must be higher than the viscous modulus in the low strain/stress plateau region of the amplitude sweep. The yield stress is then taken as the stress at the crossover of the storage modulus G' and the loss modulus G" (G'=G") and expressed in Pascal (Pa). Compositions of the present invention exhibit a yield value of about 0.1 Pa or more, or of about 0.5 Pa or more, or of about 1.0 Pa or more, or of about 2.0 Pa or more.

Compositions of the present invention exhibit suitable clarity. As used herein, the term "clarity" refers to composition ability to pass light with desire minimum light scattering. Herein, clarity is reported in terms of turbidity measured in nephelometric turbidity units (NTU), with clearer formulas having lower turbidity values. Compositions of the present invention exhibit NTU values of 95 NTU or less, or about 75 NTU or less, and or about 50 NTU or less.

Compositions of the present invention exhibit desirable mildness to the skin and eyes. As used herein, the term "mild to the skin and eyes" refers to low irritation potential and low cytotoxicity which are analyzed using the in vitro EpiDerm™ Skin Model test. The toxicity, or cell viability, is determined by measuring the relative conversion of MTT (3-[4,5-dimethylthiazol-2-yl]-2,5-diphenyltetrazolium bromide) in the tissues treated with compositions, compared to the negative/solvent control-treated tissues. Cytotoxicity is expressed as percentage with higher values corresponding to milder compositions. To test the irritation potential, the release of interleukin-1 alpha (IL-1α), a pro-inflammatory cytokine, into the tissue culture medium is measured using Enzyme Linked Immunoassay (ELISA) kits. The amount of released IL-1α expressed as pg/ml corresponds to irritation potential with lower numbers resultant in lower irritation potential. Compositions of the present invention exhibit MTT cell viability values of (measured with the EpiDerm™ Test) of about 20% or more, or of about 50% or more, or even more preferred of 70% or more, and even more preferred MTT cell viability values of (measured with the EpiDerm™ Test) of about 70% or more and IL-1alpha values (as measured with the EpiDerm™ Test) of about 800 pg/ml or less, or even more preferred of about 70% or more and of about 500 pg/ml or less, or even more preferred of about 70% or more and of about 250 pg/ml or less.

Compositions of the present invention contain one or more anionic and one or more zwitterionic surfactant(s). Preferred ratios of the weight of the anionic to the zwitterionic surfactant(s) in the composition are anionic:zwitterionic 4:1 to 1:4, more preferred of about 3:1 to 1:1, even more preferred of about 1.05:0.95 to 0.95:1.05.

Compositions of the present invention contain from about 1% to 25% by weight anionic surfactant, more preferably from about 3% to 25% by weight anionic surfactant, more preferably from about 3% to 15%, by weight even more preferable from about 3% by weight to 10% and even more preferably from about 4% to 8% by weight.

As used herein, the term "anionic surfactant" refers to a surfactant molecule bearing at least a negative charge and no positive charge besides counterion(s), $M^+$. Suitable anionic surfactants include those selected from the following classes of surfactants:

Acyl isethionates

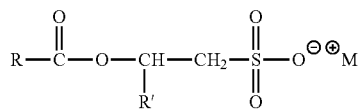

where $RCO=C_8-C_{20}$ acyl (linear or branched, saturated or unsaturated) or mixtures thereof, $R'=H$ or $CH_3$, $M^+$=monovalent cation, such as Sodium Cocoyl Isethionate ($RCO$=coco acyl, $R'=H$, $M^+=Na^+$) and Sodium Lauroyl Methyl Isethionate ($RCO$=lauroyl, $R'=CH_3$, $M^+=Na^+$).

Alkyl sulfosuccinates

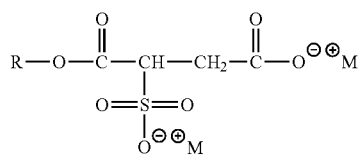

where $R=C_8-C_{20}$ alkyl (linear or branched, saturated or unsaturated) or mixtures thereof and $M^+$=monovalent cation, such as Disodium Lauryl Sulfosuccinate ($R$=lauryl, $M^+=Na^+$).

α-Sulfo fatty acid esters

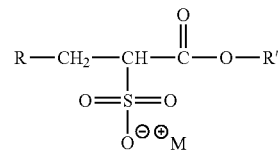

where $R=C_6-C_{16}$ alkyl (linear or branched, saturated or unsaturated) or mixtures thereof, $R'=C_1-C_2$ alkyl, and $M^+$=monovalent cation, such as Sodium Methyl 2-Sulfolaurate ($R=C_{10}H_{21}$, $R'$=methyl, $CH_3$, and $M^+=Na^+$);

α-Sulfo fatty acid salts

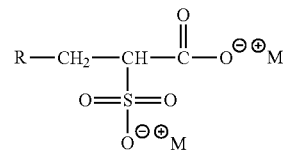

where $R=C_6-C_{16}$ alkyl (linear or branched, saturated or unsaturated) or mixtures thereof, $M^+$=monovalent cation, such as Disodium 2-Sulfolaurate ($R=C_{10}H_{21}$, $M^+=Na^+$);

Alkyl sulfoacetates

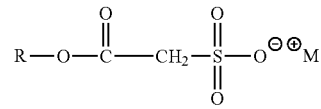

where $R=C_6-C_{18}$ alkyl (linear or branched, saturated or unsaturated) or mixtures thereof, $M^+$=monovalent cation, such as Sodium Lauryl Sulfoacetate ($R$=lauryl, $C_{12}H_{25}$, $M^+=Na^+$).

Alkyl sulfates

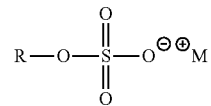

where $R=C_8-C_{20}$ alkyl (linear or branched, saturated or unsaturated) or mixtures thereof. Specific examples include TEA-Lauryl Sulfate ($R$=lauryl, $C_{12}H_{25}$, $M^+={}^+HN(CH_2CH_2OH)_3$), Sodium Lauryl Sulfate ($R$=lauryl, $C_{12}H_{25}$, $M^+=Na^+$), and Sodium Coco-Sulfate ($R$=coco alkyl, $M^+=Na^+$).

Alkyl glyceryl ether sulfonates or alkoxyl hydroxypropyl sulfonates:

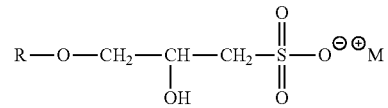

where $R=C_8-C_{24}$ alkyl (linear or branched, saturated or unsaturated) or mixtures thereof and $M^+$=monovalent cation, such as Sodium Cocoglyceryl Ether Sulfonate ($R$=coco alkyl, $M^+=Na^+$);

Alpha olefin sulfonates (AOS) prepared by sulfonation of long chain alpha olefins. Alpha olefin sulfonates consist of mixtures of alkene sulfonates,

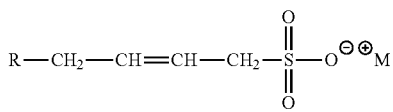

where R=$C_4$-$C_{18}$ alkyl or mixtures thereof and $M^+$=monovalent cation, and hydroxyalkyl sulfonates,

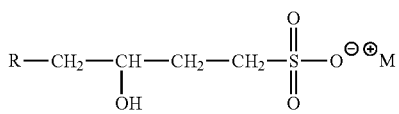

where R=$C_4$-$C_{18}$ alkyl or mixtures thereof and $M^+$=monovalent cation. Examples include Sodium C12-14 Olefin Sulfonate (R=$C_8$-$C_{10}$ alkyl, $M^+$=$Na^+$) and Sodium C14-16 Olefin Sulfonate (R=$C_{10}$-$C_{12}$ alkyl, $M^+$=$Na^+$);

Alkyl sulfonates or paraffin sulfonates:

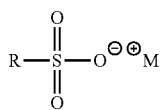

where R=$C_8$-$C_{24}$ alkyl (linear or branched, saturated or unsaturated) or mixtures thereof and $M^+$=monovalent cation. Examples include Sodium C13-17 Alkane Sulfonate (R=$C_{13}$-$C_{17}$ alkyl, $M^+$=$Na^+$) and Sodium C14-17 Alkyl Sec Sulfonate (R=$C_{14}$-$C_{17}$ alkyl, $M^+$=$Na^+$);

Alkylaryl sulfonates or linear alkyl benzene sulfonates

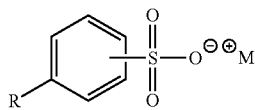

where R=$C_6$-$C_{18}$ alkyl (linear, saturated or unsaturated) or mixtures thereof and $M^+$=monovalent cation. Examples include Sodium Deceylbenzenesulfonate (R=$C_{10}$ alkyl, $M^+$=$Na^+$) and Ammonium Dodecylbenzensulfonate (R=$C_{12}$ alkyl, $M^+$=$NH_4^+$);

Alkyl ether sulfates

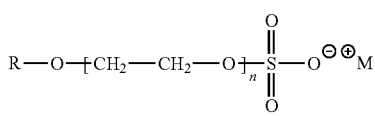

where R=$C_8$-$C_{24}$ alkyl (linear or branched, saturated or unsaturated) or mixtures thereof, n=1-12, and $M^+$=monovalent cation. Examples include Sodium Laureth Sulfate (R=$C_{12}$ alkyl, $M^+$=$Na^+$, n=1-3), Ammonium Laureth Sulfate (R=$C_{12}$ alkyl, $M^+$=$NH_4^+$, n=1-3), and Sodium Trideceth Sulfate (R=$C_{13}$ alkyl, $M^+$=$Na^+$, n=1-4);

Alkyl monoglyceride sulfates

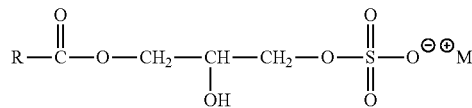

where RCO=$C_8$-$C_{24}$ acyl (linear or branched, saturated or unsaturated) or mixtures thereof and $M^+$=monovalent cation. Examples include Sodium Cocomonoglyceride Sulfate (RCO=coco acyl, $M^+$=$Na^+$) and Ammonium Cocomonoglyceride Sulfate (RCO=coco acyl, $M^+$=$NH_4^+$);

Alkyl ether carboxylates

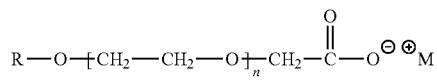

where R=$C_8$-$C_{24}$ alkyl (linear or branched, saturated or unsaturated) or mixtures thereof, n=1-20, and $M^+$=monovalent cation. Examples include Sodium Laureth-13 Carboxylate (R=$C_{12}$ alkyl, $M^+$=$Na^+$, n=13), and Sodium Laureth-3 Carboxylate (R=$C_{12}$ alkyl, $M^+$=$Na^+$, n=3);

Alkyl ether sulfosuccinates

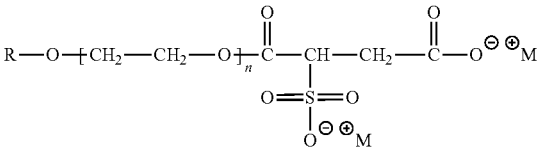

where R=$C_8$-$C_{20}$ alkyl (linear or branched, saturated or unsaturated) or mixtures thereof, n=1-12, and $M^+$=monovalent cation, such as Disodium Laureth Sulfosuccinate (R=lauryl, n=1-4, and $M^+$=$Na^+$)

Dialkyl sulfosuccinates

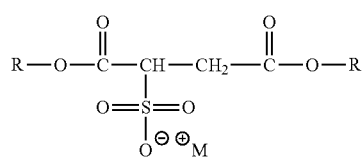

where R=$C_6$-$C_{20}$ alkyl (linear or branched, saturated or unsaturated) or mixtures thereof and $M^+$=monovalent cation, such as Diethylhexyl Sodium Sulfosuccinate (R=2-ethylhexyl, $M^+$=$Na^+$).

Alkylamidoalkyl sulfosuccinates

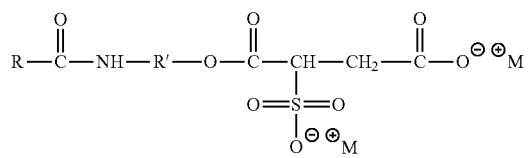

where R=$C_8$-$C_{20}$ alkyl (linear or branched, saturated or unsaturated) or mixtures thereof, R'=$C_2$-$C_4$ alkyl (linear or branched), and $M^+$=monovalent cation, such as Disodium Cocamido MIPA-Sulfosuccinate (RCO=coco acyl, R'=isopropyl, $M^+$=$Na^+$).

Alkyl sulfosuccinamates

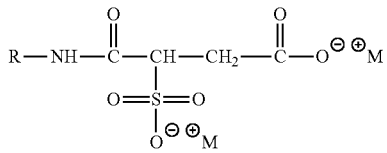

where R=$C_8$-$C_{20}$ alkyl (linear or branched, saturated or unsaturated) or mixtures thereof and $M^+$=monovalent cation, such as Disodium Stearyl Sulfosuccinamate (R=stearyl, $C_{18}H_{37}$, $M^+$=$Na^+$).

Acyl glutamates

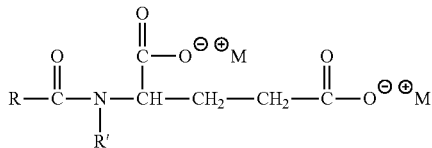

where RCO=$C_6$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, $M^+$=$Na^+$) and Disodium Lauroyl Glutamate (RCO=lauroyl, R'=H, $M^+$=$Na^+$).

Acyl aspartates

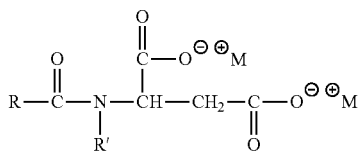

where RCO=$C_6$-$C_{20}$ acyl (linear or branched, saturated or unsaturated) or mixtures thereof, R'=H or $CH_3$, $M^+$=monovalent cation, such as Disodium N-Lauroyl Aspartate (RCO=lauroyl, R'=H, $M^+$=$Na^+$).

Acyl taurates

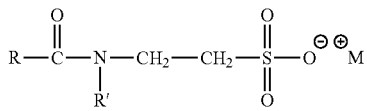

where RCO=$C_6$-$C_{20}$ acyl (linear or branched, saturated or unsaturated) or mixtures thereof, R'=H or $CH_3$, $M^+$=monovalent cation, such as Sodium Methyl Cocoyl Taurate (RCO=coco acyl, R'=$CH_3$, $M^+$=$Na^+$) and Sodium Cocoyl Taurate (RCO=lauroyl, R'=H, $M^+$=$Na^+$).

Acyl lactylates

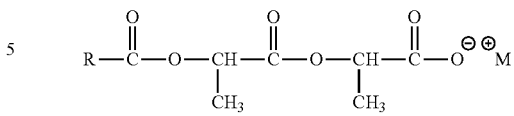

where RCO=$C_8$-$C_{20}$ acyl (linear or branched, saturated or unsaturated) or mixtures thereof, $M^+$=monovalent cation, such as Sodium Lauroyl Lactylate (RCO=lauroyl, $M^+$=$Na^+$).

Acyl glycinates and acyl sarcosinates

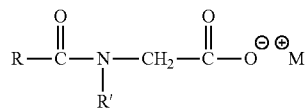

where RCO=$C_8$-$C_{20}$ acyl (linear or branched, saturated or unsaturated) or mixtures thereof, R'=H (glycinate) or $CH_3$ (sarcosinate), $M^+$=monovalent cation, such as Sodium Cocoyl Glycinate (RCO=coco acyl, R'=H, $M^+$=$Na^+$), Ammonium Cocoyl Sarcosinate (RCO=coco acyl, R'=$CH_3$, $M^+$=$NH_4^+$) and Sodium Lauroyl Sarcosinate (RCO=lauroyl, R'=$CH_3$, $M^+$=$Na^+$).

Anionic derivatives of alkyl polyglucosides, including: Sodium Lauryl Glucoside Carboxylate, Disodium Coco-Glucoside Citrate, Sodium Coco-Glucoside Tartrate, Disodium Coco-Glucoside Sulfosuccinate; Sodium Cocoglucosides Hydroxypropylsulfonate, Sodium Decylglucosides Hydroxypropylsulfonate, Sodium Laurylglucosides Hydroxypropylsulfonate; Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer; Anionic polymeric APG derivatives, such as those described in O'Lenick, U.S. Pat. Nos. 7,507,399; 7,375,064; and 7,335,627); and combinations of two or more thereof, and the like.

As used herein, the term "sulfated anionic surfactant" refers to anionic surfactants containing a —$SO_4^-M^+$ group, with $M^+$ being absent, or $H^+$ or $NH_4^+$ or $Na^+$ or $K^+$ or other monovalent or multivalent anion. Examples of sulfated anionic surfactants include, but are not limited to, sodium lauryl sulfate and sodium laureth sulfate. In certain embodiments, the compositions of the present invention are substantially free of sulfated anionic surfactant, and preferably are free of sulfated anionic surfactant.

Compositions of the present invention contain from about 1% to 25% by weight zwitterionic surfactant, more preferably from about 3% to 25% by weight zwitterionic surfactant, more preferably from about 3% to 15% by weight, even more preferable from about 3% to 10% by weight and even more preferably from about 2% to 6% by weight.

As used herein, "zwitterionic surfactant" refers to an amphiphilic molecule comprising a hydrophobic group and one or more hydrophilic groups comprising two moieties of opposite formal charges, or capable of bearing opposite formal charges (as a function of acid-base properties and solution pH). Sometimes such surfactants are also referred to as "amphoteric surfactants".

Suitable zwitterionic surfactants include, but are not limited to, surfactants described by formulas:

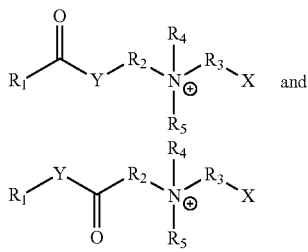

where $R_1$ is a linear, branched, saturated or unsaturated C5 to C21 hydrophobe;
$R_2$ is a linear, branched, or cyclic alkyl, hydroxyalkyl, or aromatic group;
$R_3$ is a linear or branched alkyl, hydroxyalkyl, or aromatic group;
$R_4$ is a linear or branched alkyl, hydroxyalkyl, or aromatic group;
$R_5$ is a linear or branched alkyl, hydroxyalkyl, or aromatic group; and
any of $R_2$, $R_4$, or $R_5$ can by linked in a cyclic structure; and
Y is —N(H)—, —N(R3)-, —O—, —S—; and
X is —CO2-, —SO3-, or —SO4- or phosphate or phosphonate.

Examples of zwitterionic surfactants include:
Alkylamidoalkyl betaines of the formula:

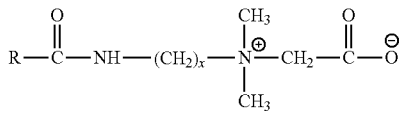

where RCO=$C_6$-$C_{24}$ acyl (saturated or unsaturated) or mixtures thereof and x=1-4. Examples include cocamidoethyl betaine (RCO=coco acyl, x=2), cocamidopropyl betaine (RCO=coco acyl, x=3), lauramidopropyl betaine (RCO=lauroyl, and x=3), myristamidopropyl betaine (RCO=myristoyl, and x=3), soyamidopropyl betaine (R=soy acyl, x=3), and oleamidopropyl betaine (RCO=oleoyl, and x=3).

Alkylamidoalkyl hydroxysultaines of the formula:

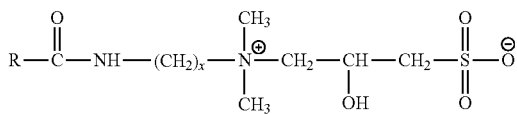

where RCO=$C_6$-$C_{24}$ acyl (saturated or unsaturated) or mixtures thereof. Examples include cocamidopropyl hydroxysultaine (RCO=coco acyl, x=3), lauramidopropyl hydroxysultaine (RCO=lauroyl, and x=3), myristamidopropyl hydroxysultaine (RCO=myristoyl, and x=3), and oleamidopropyl hydroxysultaine (RCO=oleoyl, and x=3).

Alkylamidoalkyl sultaines of the formula:

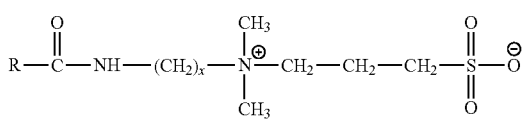

where RCO=$C_6$-$C_{24}$ acyl (saturated or unsaturated) or mixtures thereof. Examples include cocamidopropyl sultaine (RCO=coco acyl, x=3), lauramidopropyl sultaine (RCO=lauroyl, and x=3), myristamidopropyl sultaine (RCO=myristoyl, and x=3), soyamidopropyl betaine (RCO=soy acyl, x=3), and oleamidopropyl betaine (RCO=oleoyl, and x=3).

Amphoacetates of the formula:

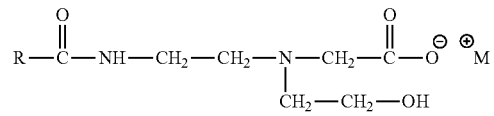

where RCO=$C_6$-$C_{24}$ acyl (saturated or unsaturated) or mixtures thereof and $M^+$=monovalent cation. Examples include sodium lauroamphoacetate (RCO=lauroyl and $M^+$=$Na^+$) and sodium cocoamphoacetate (RCO=coco acyl and $M^+$=$Na^+$).

Amphodiacetates of the formula:

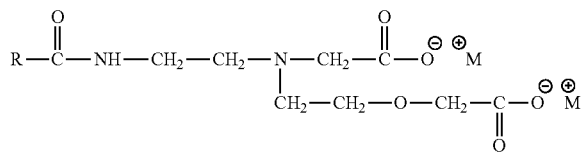

where RCO=$C_6$-$C_{24}$ acyl (saturated or unsaturated) or mixtures thereof and $M^+$=monovalent cation. Examples include disodium lauroamphodiacetate (RCO=lauroyl and M=$Na^+$) and disodium cocoamphodiacetate (RCO=coco acyl and M=$Na^+$).

Amphopropionates of the formula:

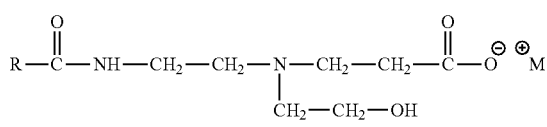

where RCO=$C_6$-$C_{24}$ acyl (saturated or unsaturated) or mixtures thereof and $M^+$=monovalent cation. Examples include sodium lauroamphopropionate (RCO=lauroyl and $M^+$=$Na^+$) and sodium cocoamphopropionate (RCO=coco acyl and $M^+$=$Na^+$).

Amphodipropionates of the formula:

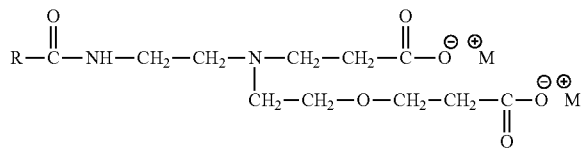

where RCO=$C_6$-$C_{24}$ acyl (saturated or unsaturated) or mixtures thereof and $M^+$=monovalent cation. Examples include disodium lauroamphodipropionate (RCO=lauroyl and = $Na^+$) and disodium cocoamphodipropionate (RCO=coco acyl and $M^+$=$Na^+$).

Amphohydroxypropylsulfonates of the formula:

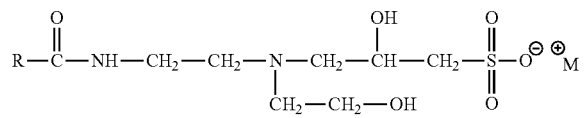

where $RCO=C_6-C_{24}$ acyl (saturated or unsaturated) or mixtures thereof and $M^+$=monovalent cation, such as sodium lauroamphohydroxypropylsulfonate ($RCO$=lauroyl and $M^+=Na^+$) and sodium cocoamphohydroxypropylsulfonate ($RCO$=coco acyl and $M^+=Na^+$).

Other examples include amphohydroxyalkylphosphates and alkylamidoalkyl amine oxides.

Compositions of the present invention contain a Superhydrophilic Amphiphilic Copolymer (SAC). According to certain embodiments, the SAC is used in a concentration from greater than about 0.1% to about 30% by weight of active SAC in the composition. Preferably, the SAC is in a concentration from about 0.5 to about 20% by weight of active, more preferably from about 1 to about 15% by weight of active, even more preferably from about 2 to about 10% by weight of active of active SAC in the composition. In certain other preferred embodiments, the compositions of the present invention comprise from about 0.5 to about 15% by weight of active, more preferably from about 3 to about 15% by weight of active or from about 1.5% to about 10% by weight of active SAC in the composition.

As used herein, the term "superhydrophilic amphiphilic copolymer," ("SAC") is defined as a copolymer that may be represented by the following general structure:

wherein an "SRU" is a superhydrophilic repeat unit as defined herein, an "ARU" is an amphiphilic repeat unit as defined herein, an "HRU" is a hydrophilic repeat unit as defined herein, wherein s≥2, a>0, h≥0, and the total number of repeat units, s+a+h is between 4 and about 1000. The term "between," when used herein to specify a range such as "between 4 and about 1000," is inclusive of the endpoints, e.g. "4" and "about 1000." The total number of repeat units in the SAC is based on the weight-average molecular weight ($M_w$) of the SAC; thus the number of repeat units, as discussed herein are "weight average" as well. Further, all molecular weights described herein are in the units of Daltons (Da). As will be recognized by one of skill in the art, the pattern of repeat units (SRUs, ARUs, HRUs) incorporated in SACs of the present invention are generally random; however, they may also have alternating, statistical, or blocky incorporation patterns. In addition, SAC architectures may be linear, star-shaped, branched, hyperbranched, dendritic, or the like.

Those of skill in the art will recognize that total number of repeat units in a SAC (SRUs+ARUs+HRUs, i.e. s+a+h in the above formula) is synonymous with the term "degree of polymerization" ("DP") of the SAC.

A "repeat unit" as defined herein and known the art is the smallest atom or group of atoms (with pendant atoms or groups, if any) comprising a part of the essential structure of a macromolecule, oligomer, block, or chain, the repetition of which constitutes a regular macromolecule, a regular oligomer molecule, a regular block, or a regular chain (definition from Glossary of Basic Terms in Polymer Science, A. D. Jenkins et al. *Pure Appl. Chem.* 1996 68, 2287-2311.) As will be recognized by those of skill in the art in light of the description herein and knowledge of the art, the backbone of a polymer derived from ethylenically-unsaturated monomers comprises repeat units including one or two, or in the case of alternating polymers four, carbon atoms that were unsaturated in the monomers prior to polymerization, and any pendant groups of such carbons. For example, polymerization of an ethylenically-unsaturated monomer of the formula: $(A)(Y)C=C(B)(Z)$ will generally result in a polymer comprising repeat units of the formula:

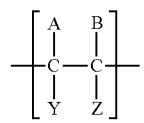

comprising the two previously unsaturated carbons of the monomer and their pendant groups (examples of which are described herein below, for example in the descriptions of SRUs, ARUs, and HRUs). However, if the pendant groups of the two carbons are the same such that, for example in the formula above, A—C—Y and B—C—Z are the same moiety, then each of such one carbon units and its pendant groups (A-C—Y or B—C—Z, being the same) are considered to be the repeat unit comprising only one previously unsaturated carbon from the monomer (e.g. the repeat unit of a homopolyer derived from ethylene, $H_2C=CH_2$ is $[—[CH_2]—]$ not $[—[CH_2CH_2]—]$. With regard only to alternating copolymers, which as known in the art are defined as those polymers in which the repeat units derived from the two comonomers alternate consistently throughout the polymer (as opposed to the random polymerization of co-monomers to form a polymer in which repeat units derived from the two monomers are randomly linked throughout the polymer or the block copolymerization of comonomers to form non-alternating blocks of repeat units derived from the two monomers), the repeat unit is defined as the unit derived from one of each of the co-monomers comprising four carbons that were previously ethylenically-unsaturated in the two comonomers prior to polymerization. That is, maleic anhydride and vinyl methyl ether are used in the art to form an alternating copolymer, poly(maleic anhydride-alt-vinyl methyl ether) having repeat units of the structure:

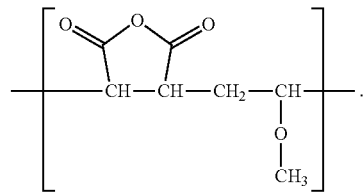

For saccharide-based polymers whose backbone is formed by linking sugar rings, the repeat unit generally comprises the sugar ring and pendant groups (as shown herein below, for example in the descriptions of SRUs, ARUs, and HRUs.) Examples of such repeat units also include sugar ring repeat units with pendant sugar rings, for example, Glactomannans are polysaccharides comprised of a mannose (monosaccharide-based) backbone. Pending from some but not all of the mannose groups in the backbone (and arranged in either a random or block fashion) are pendant galactose groups. As will be readily understood by one skilled in the art, this structure is best described as having, two repeat units, mannose and mannose-galactose.

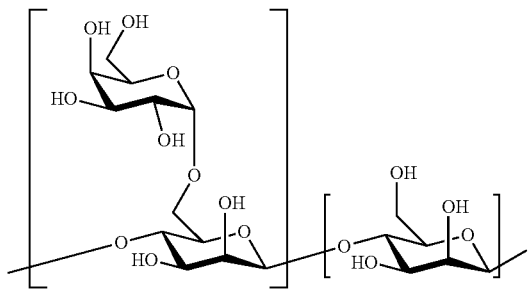

For alternating saccharide-based polymers, then the repeat unit is the two sugar rings derived from the alternating sugar-based monomers and their pendant groups. For example, Hyaluronan is an alternating saccharide copolymer derived from two saccharides, D-glucuronic acid and D-N-acetylglucosamine that alternate to give a disaccharide repeat units.

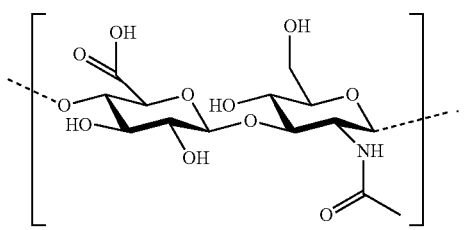

As used herein, the term "superhydrophilic repeat unit," ("SRU") is defined as a repeat unit that comprises two or more hydrophilic moieties and no hydrophobic moieties. For example, SRUs may be derived from ethylenically-unsaturated monomers having two or more hydrophilic moieties and no hydrophobic moieties, including repeat units of the general formulae:

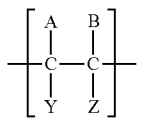

wherein A, B, Y, and Z collectively include at least two hydrophilic moieties and no hydrophobic moieties; or

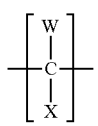

wherein W and X collectively include at least two hydrophilic moieties. Illustrative examples of such SRUs include, but are not limited to, those derived from superhydrophilic monomers described herein and the like, such as:

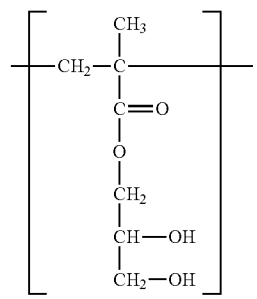

which is derived from glyceryl methacrylate; or others such as:

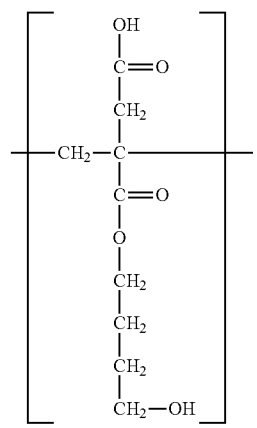

which is derived from 4-Hydroxybutyl itaconate; and the like.

Other examples of SRUs include saccharide-based repeat units including repeat units derived from fructose, glucose, galactose, mannose, glucosamine, mannuronic acid, guluronic acid, and the like, such as:

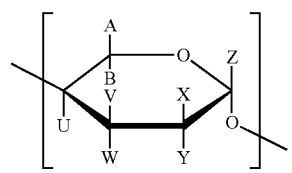

wherein A, B, U, V, W, X, Y, and Z collectively include at least two hydrophilic moieties and no hydrophobic moieties, one example of which includes

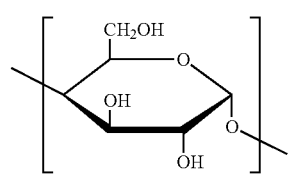

which is a α(1→4)-D-glucose SRU; or

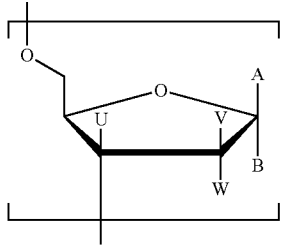

wherein A, B, U, V, and W collectively include at least two hydrophilic moieties and no hydrophobic moieties, one example of which includes

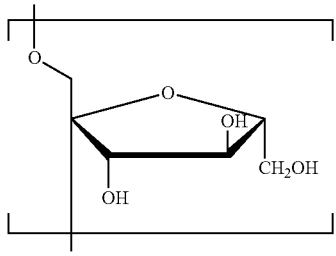

a α(2→1)-D-fructose SRU; and the like. As will be recognized by those of skill in the art, monosaccharide repeat units may be linked in various fashions, that is, through various carbons on the sugar ring e.g. (1→4), (1→6), (2→1), etc. Any of such linkages, or combinations thereof, may be suitable for use herein in monosaccharide SRUs, ARUs, or HRUs.

Other examples of SRUs include repeat units derived from amino acids, including, for example, repeat units of the formula:

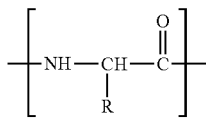

wherein R includes a hydrophilic repeat unit, examples of which include

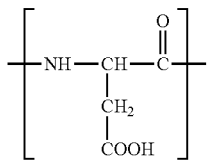

an aspartic acid SRU, and the like.

As used herein, the term "amphiphilic repeat unit," ("ARU") is defined as a repeat unit that comprises at least one hydrophilic moiety and at least one hydrophobic moiety. For example, ARUs may be derived from ethylenically-unsaturated monomers having at least one hydrophilic moiety and at least one hydrophobic moiety, including repeat units of the general formulae

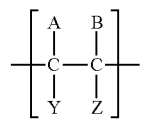

wherein A, B, Y, and Z collectively include at one hydrophilic moiety and at least one hydrophobic moiety; or

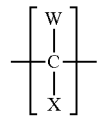

wherein W and X collectively include at one hydrophilic moiety and at least one hydrophobic moiety; examples of which include

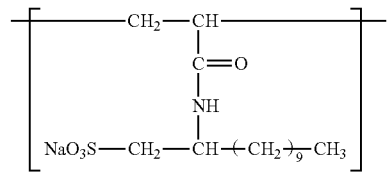

sodium 2-acrylamidododecylsulfonate amphiphilic repeat unit (ARU), and the like.

Other examples of ARUs include saccharide-based repeat units including repeat units derived from including repeat units derived from fructose, glucose, galactose, mannose, glucosamine, mannuronic acid, guluronic acid, and the like, such as:

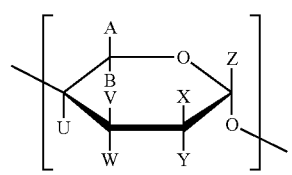

wherein A, B, U, V, W, X, Y, and Z collectively include at least one hydrophilic moiety and at least one hydrophobic moiety, or

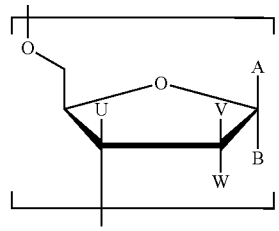

wherein A, B, U, V, and W collectively include at least one hydrophilic moiety and at least one hydrophobic moiety, examples of which include

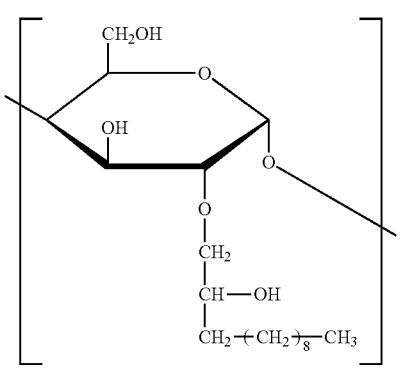

1,2-epoxydodecane modified α(1→4)-D-glucose ARU, and the like.

Other examples of ARUs include repeat units derived from amino acids, including, for example, repeat units of the formula:

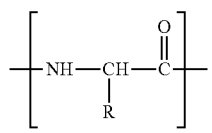

wherein R includes a hydrophobic group, examples of which include

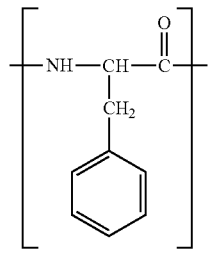

a phenylalanine ARU; and the like.

As will be readily understood by those of skill in the art, the term "hydrophilic repeat unit," ("HRU") is defined as a repeat unit that comprises one and only one hydrophilic moiety and no hydrophobic moieties. For example, HRUs may be derived from ethylenically-unsaturated monomers having one and only one hydrophilic moiety and no hydrophobic moieties, including repeat units of the general formulae

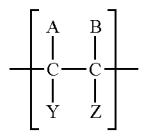

wherein A, B, Y, and Z collectively include one and only one hydrophilic moiety and no hydrophobic moieties; or

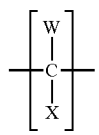

wherein W and X collectively include one and only one hydrophilic moiety and no hydrophobic moieties, examples of which include

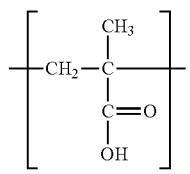

methacrylic acid hydrophilic repeat unit (HRU); and the like.

Other examples of HRUs include saccharide-based repeat units including repeat units derived from fructose, glucose, galactose, mannose, glucosamine, mannuronic acid, guluronic acid, and the like, such as:

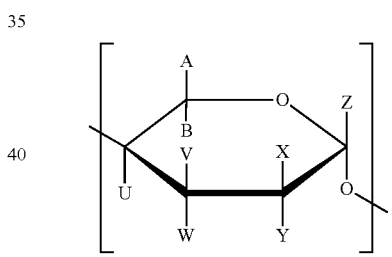

wherein A, B, U, V, W, X, Y, and Z collectively include one and only one hydrophilic moiety and no hydrophobic moieties, or

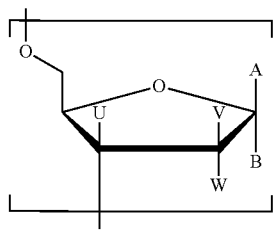

wherein A, B, U, V, and W collectively include one and only one hydrophilic moiety and no hydrophobic moieties. One example of saccharide-based hydrophilic repeat unit includes methylcellulose HRU, (methyl-substituted poly[α(1→4)-D-glucose], DS=2.0)

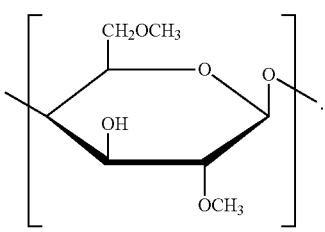

Other examples of HRUs include repeat units derived from amino acids, including, for example, repeat units of the formula:

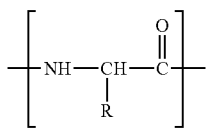

wherein R is neither a hydrophilic nor hydrophobic moiety, one example of which includes

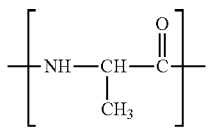

alanine HRU; and the like. As will be recognized by one of skill in the art, in any of the formulae herein, examples of moieties that are neither hydrophilic nor hydrophobic include hydrogen, $C_1$-$C_3$ alkyl, $C_1$-$C_3$ alkoxy, $C_1$-$C_3$ acetoxy, and the like.

Compositions of the present invention contain organic acid. Suitable organic acids include any cosmetically acceptable organic acid. Suitable organic acids include, but are not limited to, for example: citric acid, acetic acid, benzoic acid, salicylic acid, glycolic acid, lactic acid, malic acid, tartaric acid, combinations of two or more thereof or the like.

Any suitable amount of organic acid may be used in the compositions of the present invention. In certain embodiments, the compositions comprise from about 0.05% to about 5% by weight, more preferably from about 0.1% to about 2.5t % by weight, and even more preferably from about 0.25% to about 2% by weight of organic acid.

In certain embodiments of the present invention, the composition may further comprise a nonionic surfactant. As used herein, the term "nonionic surfactant" refers to a surfactant molecule bearing no electrostatic charge. Any of a variety of nonionic surfactants is suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 sorbitan laurate is a sorbitan monoester of lauric acid ethoxylated with an average of about 80 moles of ethylene oxide. Polysorbate 20 is the laurate monoester of a mixture of sorbitol and sorbitol anhydrides condensed with approximately 20 moles of ethylene oxide.

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is decyl glucoside, which is the condensation product of decyl alcohol with a glucose oligomer.

Another class of suitable nonionic surfactants includes polyglycerol nonionic surfactant. Examples of polyglycerol nonionic surfactants include, but are not limited to, polyglycerol esters (PGEs), such as polyglycerol-10 laurate.

As used herein, the term "polyglyceryl nonionic surfactant" means an amphiphilic molecule comprising one or more nonionic hydrophilic segments comprised of a polyglyceryl moiety and one or more hydrophobic moieties. Examples of polyglyceryl nonionic surfactants include, but are not limited to, polyglyceryl esters (PGEs), such as polyglyceryl-10 laurate where PG=polyglyceryl moiety comprising ten (10) glyceryl repeat units, and R=$C_{11}H_{23}$:

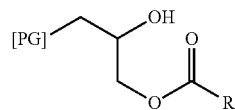

as well as, polyglyceryl-10 caprylate/caprate, polyglyceryl-10 cocoate, polyglyceryl-10 myristate, polyglyceryl-10 palmitate, polyglyceryl-10 oleate, polyglyceryl-12 laurate, and the like. PGEs of the present invention may include polyglyceryl moieties bearing multiple ester substitutions (i.e. the PGEs may be monoesters, diesters, triesters, etc.). Other polyglyceryl nonionic surfactants include polyglyceryl ethers, such as polyglyceryl-10 lauryl ether, where PG=polyglyceryl moiety comprising 10 glyceryl repeat units, and R=$C_{12}H_{25}$:

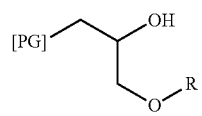

and the like. Still other polyglyceryl nonionic surfactants include polyglyceryl sorbitan fatty acid esters, such as polyglyceryl-20 sorbitan laurate, where PG=polyglycerol, the sum of all PG RUs=20, and R=$C_{11}H_{23}$. (see Bevinakatti, et al. WO 2009016375, assigned to Croda International PLC)

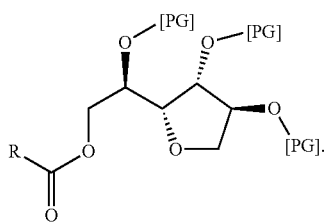

Any suitable polyglyceryl nonionic surfactants may be used in the compositions of the present invention. In certain preferred embodiments, the polyglyceryl nonionic surfactants are selected from the group consisting of polyglyceryl esters, polyglyceryl ethers, polyglyceryl sorbitan fatty acid esters, combinations of two or more thereof and the like. In certain more preferred embodiments, the polyglyceryl nonionic surfactants are selected from the group consisting of polyglyceryl esters, polyglyceryl ethers, and combinations of two or more thereof. In certain other preferred embodiments, the compositions of the present invention comprise one or more polyglyceryl nonionic surfactants selected from the group consisting of: polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof.

In preferred embodiments, the polyglyceryl nonionic surfactants used in the present invention have a total combined glyceryl degree of polymerization (DP) (i.e. total of all glyceryl repeat units in a given molecule) of from about 4 to about 40 repeat units. In certain more preferred embodiments, the polyglyceryl nonionic surfactants have a DP of from about 6 to about 30, more preferably from about 6 to about 20, more preferably, from about 6 to about 15, and more preferably from about 6 to about 12 glyceryl repeat units.

Any suitable amount of polyglyceryl nonionic surfactant may be used in the compositions of the present invention. In certain embodiments, the compositions comprise from greater than zero to about 25% by weight of polyglyceryl nonionic surfactant. In certain preferred embodiments, the compositions comprise from about 0.05 wt % to about 20 wt %, more preferably from about 0.1 wt % to about 15 wt %, and even more preferably from about 0.2 wt % to about 10 wt %, and still more preferably from about 0.25 wt % to about 5 wt % of total polyglyceryl nonionic surfactant.

Another class of suitable nonionic surfactants includes alkanolamides, like cocamide MEA and cocamide DEA.

In certain embodiments of the present invention, the composition may further comprise an inorganic salt. Inorganic salts that are suitable for use in this invention include, but are not limited to, sodium chloride, potassium chloride, sodium bromide, potassium bromide, ammonium chloride, ammonium bromide and other mono-valent as well as multivalent ion containing salts. Typically, compositions of the present invention will comprise from about 0.05% to about 6% w/w of inorganic salt, or from about 0.1% to about 4% w/w of inorganic salt, or from about 0.1% to about 2% w/w of inorganic salt, or from about 0.1% to about 1.5% w/w of inorganic salt.

The pH of compositions of the present invention is adjusted to preferably from about 3 to about 6.5, more preferably from about 3 to about 6, more preferably from about 3 to about 5.5, more preferably from about 3 to about 5, and most preferably from about 3 to about 4.5. The pH of the composition may be adjusted as low as 3 provided that formula stability and performance (e.g. foaming, mildness and viscosity) are not negatively affected. The pH of the composition may be adjusted to the appropriate acidic value using any cosmetically acceptable organic or inorganic acid, such as citric acid, acetic acid, glycolic acid, lactic acid, malic acid, tartaric acid, hydrochloric acid, combinations of two or more thereof or the like.

The Brookfield viscosity (see below for definition) of composition of the present invention is preferably below about 100,000 cps, more preferably below about 80,000, more preferably from about 3,000 to about 80,000, more preferably from about 3,000 to about 50,000.

In certain embodiments of the present invention, the composition may further comprise a cationic surfactant. Classes of cationic surfactants that are suitable for use in this invention include, but are not limited to, alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred. In certain embodiments of the present invention, the composition comprises cationic conditioning polymers. Examples of suitable cationic conditioning polymers include cationic cellulose and its derivatives; cationic guar and its derivatives; and diallyldimethylammonium chloride. The cationic cellulose derivative may be a polymeric quaternary ammonium salt derived from the reaction of hydroxyethyl cellulose with a trimethylammonium substituted epoxide, known as Polyquaternium-10. The cationic guar derivative may be a guar hydroxypropyltrimonium chloride. Other useful cationic conditioning polymers are those derived from the monomer diallyldimethylammonium chloride. The homopolymer of this monomer is Polyquaternium-6. The copolymer of diallyldimethylammonium chloride with acrylamide is known as Polyquatemium-7. Other suitable conditioning polymers include those disclosed in U.S. Pat. No. 5,876,705, which is incorporated herein by reference.

The composition of this invention may further contain any other ingredients or additives typically used in personal care products, e.g., dermatological or in cosmetic formulations, including active ingredients. Examples of further ingredients or additives are surfactants, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, solvents, viscosity controlling agents and opacifying agents, and the like, provided that they are physically and chemically compatible with the other components of the composition. Active ingredients may include, without limitation, anti-inflammatory agents, anti-bacterials, anti-fungals, anti-itching agents, moisturizing agents, plant extracts, vitamins, and the like. Also included are sunscreen actives which may be inorganic or organic in nature. Of particular interest are any active ingredients suited for topical application of personal care compositions.

Examples of thickeners and rheology modifiers, include but are not limited to, naturally-derived polysaccharides including xanthan gum, dehydroxanthan gum, *Cyamopsis tetragonoloba* (guar) gum, cassia gum, *Chondrus crispus* (carrageenan) gum, alginic acid and alginate gums (e.g. algin, calcium alginate, etc.), gellan gum, pectin, microcrystalline cellulose, nonethoxylated derivatives of cellulose (e.g. sodium carboxymethylcellulose, hydroxypropyl methylcellulose, etc.), and hydroxypropyl guar, as well as micellar thickeners, such as: cocamide MIPA, lauryl lactyl lactate, or sorbitan sesquicaprylate, and combinations of two or more thereof and the like.

Examples of preservatives and preservative boosters include but are not limited to organic acids (like e.g. benzoic acid, lactic acid, salicylic acid), benzyl alcohol, caprylyl glycol, decylene glycol, ethylhexylglycerin, gluconolactone, methylisothiazolinone, and combinations of two or more thereof, and the like.

The following examples are meant to illustrate the present invention, not to limit it thereto.

EXAMPLES

Test methods used in the Examples are described as follows:
Clarity Test:

The clarity of the cleansing compositions was determined via turbidity measurements on a HF Scientific Micro 1000 Turbidimeter with white light source operating at ambient temperature (22° C.±1° C.). Clarity is reported in terms of turbidity measured in nephelometric turbidity units (NTU), with clearer formulas having lower turbidity values.
Yield Stress Measurements:

Yield stress measurements were performed in a TA Instruments (New Castle, Del.) ARES G2 strain-controlled rheometer equipped with a Peltier temperature control system at 25° C. The yield stress was measured by performing an amplitude sweep oscillatory test where the strain amplitude was increased logarithmically from 0.01 or 0.1 to 1000% strain at an angular frequency of 0.1 radians per second. The elastic and viscous moduli (also referred to as storage and loss moduli), G' and G", respectively, were then plotted versus the oscillatory stress. To possess a yield stress at a given angular frequency, the elastic modulus must be higher than the viscous modulus in the low strain/stress plateau region of the amplitude sweep. The yield stress is then taken as the stress at the crossover where G'=G", which is the transition point from solid-dominated to liquid-dominated behavior upon increasing stress.
Brookfield Viscosity Measurements:

All Brookfield viscosity values reported in this patent are measured with a Brookfield viscometer DV-II+ PRO using RVT spindle #5 at 5 rpm and a value read after 1 minute. Measurements are done in a 4 oz glass jar at 22 degree Celsius.
EpiDerm™ Test:

Upon receipt of the EpiDerm™ Skin Kit (MatTek Corporation), the solutions were stored as indicated by the manufacturer. The EpiDerm™ tissues were stored at 2-8° C. until use. On the day of dosing, EpiDerm™ Assay Medium was warmed to approximately 37° C. Nine-tenths mL of Assay Medium were aliquotted into the appropriate wells of 6-well plates. The 6-well plates were labeled to indicate test article and exposure time. Each EpiDerm™ tissue was inspected for air bubbles between the agarose gel and cell culture insert prior to opening the sealed package. Tissues with air bubbles covering greater than 50% of the cell culture insert area were not used. The 24-well shipping containers were removed from the plastic bag and their surfaces were disinfected with 70% ethanol.

The EpiDerm™ tissues were transferred aseptically into the 6-well plates. The EpiDerm™ tissues were then incubated at 37±1° C. in a humidified atmosphere of 5±1% $CO_2$ in air (standard culture conditions) for at least one hour. The medium was aspirated and 0.9 mL of fresh Assay Medium were added to each assay well below the EpiDerm™ tissues. The plates were returned to the incubator until treatment was initiated. Upon opening the bag, any remaining unused tissues were briefly gassed with an atmosphere of 5% $CO_2$/95% air and placed back at 2-8° C. for later use. The test articles were administered to the test system as 10% w/v dilutions in sterile, deionized water. Each test article dilution was prepared by weighing approximately 1,000 mg of the test article into a pre-labeled conical tube. Sterile, deionized water was added until a 10% w/v dilution was achieved and the tube was vortexed for approximately 1 minute prior to application. In the following, each test article dilution is referred to as the test article.

The test articles were tested in duplicate EpiDerm™ tissues at four exposure times of 4, 8, 16, and 24 hours. One hundred microliters of each test article were applied to each EpiDerm™ tissue. The negative control, 100 µL of sterile, deionized water, was treated in duplicate tissues for 1, 4, 16, and 24 hours. The positive control, 100 µL of 1% Triton®-X-100 (Fisher), was treated in duplicate tissues for 4 and 8 hours. The treated tissues were then incubated at standard culture conditions for the appropriate exposure time. Two sets of dilutions were prepared for the study: one set for the 4, 8, and 24 hours treatment and one set for the 16 hours treatment. A 1.0 mg/mL solution of MTT in warm MTT Addition Medium was prepared no more than 2 hours before use. After the appropriate exposure time, the EpiDerm™ tissues were extensively rinsed with Calcium and Magnesium-Free Dulbecco's Phosphate Buffered Saline ($Ca^{2+}$ $Mg^{2+}$-Free DPBS) and the wash medium was decanted. Three-tenths mL of MTT reagent were added to designated wells in a prelabeled 24-well plate. The EpiDerm™ tissues were transferred to the appropriate wells after rinsing. The plates were incubated for approximately three hours at standard culture conditions. After the incubation period with MTT solution, the EpiDerm™ tissues were blotted on absorbent paper, cleared of excess liquid, and transferred to a prelabeled 24-well plate containing 2.0 mL of isopropanol in each designated well. The plates were covered with parafilm and stored in the refrigerator (2-8° C.) until the last exposure time was harvested. Then the plates were shaken for at least two hours at room temperature. At the end of the extraction period, the liquid within the cell culture inserts was decanted into the well from which the cell culture insert was taken. The extract solution was mixed and 200 µL were transferred to the appropriate wells of a 96-well plate. Two hundred µL of isopropanol were placed in the two wells designated as the blanks. The absorbance at 550 nm (OD550) of each well was measured with a Molecular Devices' Vmax plate reader.

The raw absorbance values were captured. The mean OD550 value of the blank wells was calculated. The corrected mean OD550 value of the negative control(s) was determined by subtracting the mean OD550 value of the blank wells from their mean OD550 values. The corrected OD550 value of the individual test article exposure times and the positive control exposure times was determined by subtracting the mean OD550 value of the blank wells from their OD550 values.

Corr. test article exposure time $OD_{550}$=Test article exposure time $OD_{550}$–Blank mean $OD_{550}$ The following percent of control calculations were made:

$$\% \text{ Viability} = \frac{\text{Final corrected } OD_{550} \text{ of Test Article or Positive Control}}{\text{corrected mean } OD_{550} \text{ of Negative Control}} \times 100$$

The individual % of control values were then averaged to calculate the mean % of control per exposure time. Test article and positive control viability calculations were performed by comparing the corrected OD550 values of each test article or positive control exposure time to a relevant negative control.

Exposure time response curves were plotted with the % of Control on the ordinate and the test article or positive control exposure time on the abscissa. The ET50 value was interpolated from each plot. To determine the ET50, the two consecutive points were selected, where one exposure time resulted in a relative survival greater than 50%, and one exposure time resulted in less than 50% survival. The two select exposures were used to determine the slope and the y-intercept for the equation y=m(x)+b. Finally, to determine the ET50, the equation was solved for y=50. If all of the exposure times showed greater than 50% survival, the ET50 value was presented as greater than the maximum exposure time.

Homogeneity Test (Stability Test):

The composition is visually inspected after preparation. Besides suspended insoluble components (like e.g. scrubbing beads, mica particles), no inhomogeneities should be detectable. This is referred to as a homogeneous 1-phase system. The sealed composition is placed for at least 48 hours at a temperature of –22 degree Celsius. The composition is visually inspected. If macroscopic changes can be detected (formation of layers, fracking or other forms of macroscopic phase separation), the composition is considered not homogeneous.

Polymers (E1-E5) used in Inventive Compositions and polymers used in Comparative Compositions (C1-C12):

Acrylates Copolymer (Inventive Example 1) was obtained from Dow as Aculyn™ Excel. Acrylates Crosspolymer-4 (Inventive Example 2, 4 and 5, and Comparative Example 7), as well as Acrylates/C10-30 Alkyl Acrylate Crosspolymer (Comparative Example 2), and Polyacrylate-1 Crosspolymer (Comparative Example 5) were obtained from Lubrizol as Carbopol® Aqua SF-2, Pemulen™ TR-2 and Carbopol® Aqua CC, respectively. Acrylates/Aminoacrylates/C10-30 Alkyl PEG-20 Itaconate Copolymer (Inventive Example 3) and Acrylates/Steareth-20 Itaconate Copolymer (Comparative Example 4) were obtained from Akzo Nobel Personal Care as Structure® PLUS and Structure® 2001, respectively. Carbomer (Comparative Example 1) was obtained from Evonik Inc. as TEGO® Carbomer 841 SER, and Polyacrylate Crosspolymer-6 (Comparative Example 3) was obtained from SEPPIC as SEPIMAX™ ZEN.

TABLE 1a

| Material, INCI | Trade Name | Activity (%) | E1 wt. % | E2 wt. % | E3 wt. % | C1 wt. % | C2 wt. % | C3 wt. % | C4 wt. % | C5 wt. % |
|---|---|---|---|---|---|---|---|---|---|---|
| Sodium Hydrolyzed Potato Starch Dodecenylsuccinate | NATRASURF™ PS-111 | 100 | 2.50 | 2.50 | 2.50 | 2.50 | 2.50 | 2.50 | 2.50 | 2.50 |
| Acrylates Copolymer | Aculyn Excel | 30 | 0.9 | | | | | | | |
| Acrylates Crosspolymer-4 | Carbopol® Aqua SF-2 | 32 | | 1.2 | | | | | | |
| Acrylates/ Aminoacrylates/ C10-30 Alkyl PEG-20 Itaconate Copolymer | Structure® PLUS | 20 | | | 1.5 | | | | | |
| Carbomer | Tego Carbomer 841SER | 100 | | | | 0.5 | | | | |
| Acrylates/C10-30 Alkyl Acrylate Crosspolymer | Pemulen™ TR-2 | 100 | | | | | 0.5 | | | |
| Polyacrylate Crosspolymer-6 | SepiMAX ZEN | 100 | | | | | | 0.5 | | |
| Acrylates/Steareth-20 Itaconate Copolymer | Structure® 2001 | 20 | | | | | | | 1.5 | |
| Polyacrylate-1 Crosspolymer | Carbopol® Aqua CC | 30 | | | | | | | | 1.2 |
| Cocamidopropyl Hydroxysultaine | Mirataine® CBS | 42* | 6.00 | 6.00 | 6.00 | 6.00 | 6.00 | 6.00 | 6.00 | 6.00 |
| Sodium C14-16 Olefin Sulfonate | Rhodacal 246 FF | 44* | 6.00 | 6.00 | 6.00 | 6.00 | 6.00 | 6.00 | 6.00 | 6.00 |
| Salicylic Acid | Salicylic Acid PHA | 100 | 2.00 | 2.00 | 2.00 | 2.00 | 2.00 | 2.00 | 2.00 | 2.00 |
| Citric Acid solution | Citric Acid | 20 | Q.S. to pH 4.0 | Q.S. to pH 4.0 | Q.S. to pH 4.0 | Q.S. to pH 4.0 | Q.S. to pH 4.0 | Q.S. to pH 4.0 | Q.S. to pH 4.0 | Q.S. to pH 4.0 |

TABLE 1a-continued

| Material, INCI | Trade Name | Activity (%) | E1 wt. % | E2 wt. % | E3 wt. % | C1 wt. % | C2 wt. % | C3 wt. % | C4 wt. % | C5 wt. % |
|---|---|---|---|---|---|---|---|---|---|---|
| Tetrasodium EDTA | Versene NA | 100 | 0.10 | 0.10 | 0.10 | 0.10 | 0.10 | 0.10 | 0.10 | 0.10 |
| Glycerin | | 100 | 2.00 | 2.00 | | | | | | |
| Sorbitol | | 70 | | | 3.01 | 3.01 | 3.01 | 3.01 | 3.01 | 3.01 |
| Sodium Hydroxide solution (20%) | Sodium Hydroxide | 20 | Q.S. | Q.S. | Q.S. | Q.S. | Q.S. | Q.S. | Q.S. | Q.S. |
| Water | Purified Water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

*Activity in water. The aqueous phase may also contain some amounts of sodium chloride and impurities, such as fatty acid, fatty alcohol or fatty amine.

TABLE 1b

| INCI | Trade Name | Activity (%) | C6 wt. % | C7 wt. % | C8 wt. % | E4 wt. % | E5 wt. % |
|---|---|---|---|---|---|---|---|
| Acrylates Crosspolymer-4 | Carbopol ® Aqua SF-2 Polymer | 32 | | 1.50 | | 1.50 | 1.50 |
| Sodium Hydrolyzed Potato Starch Dodecenylsuccinate | NATRASURF ™ PS-111 | 100 | | | 2.00 | 2.50 | 2.50 |
| Weight ratio zwitterionic/amphoteric to anionic surfactant (active to active) | | | 1.00 | 1.00 | 1.00 | 1.00 | 1.00 |
| Zwitterionic (weight % active) | | | | | | | |
| Cocamidopropyl Hydroxysultaine | Mirataine ® CBS | 42* | 6.00 | 6.00 | 6.00 | 6.00 | 6.00 |
| Anionic (weight % active) | | | | | | | |
| Sodium C14-16 Olefin Sulfonate | Rhodacal 246 FF | 44* | 6.00 | 6.00 | 6.00 | 6.00 | 6.00 |
| Organic Acids | | | | | | | |
| Salicylic Acid | Salicylic Acid PHA | 100 | 2.00 | 2.00 | 2.00 | 2.00 | |
| Citric Acid | Citric Acid | 20 | Q.S. to pH 4.0 | Q.S. to pH 4.0 | Q.S. to pH 4.0 | Q.S. to pH 4.0 | Q.S. to pH 4.5 |
| Other | | | | | | | |
| Glycerin | Moon Glycerin USP/FCC | 100 | 2.00 | 2.00 | 2.00 | | |
| Sorbitol | Sorbitol USP/FCC | 70 | | | | 3.01 | 3.01 |
| Tetrasodium EDTA | Versene NA | 100 | 0.10 | 0.10 | 0.10 | 0.10 | 0.10 |
| Sodium Benzoate | Sodium Benzoate, NF, FCC | 100 | | | | | 0.50 |
| Sodium Hydroxide solution (20%) | Sodium Hydroxide Pellets NF, FCC | 20 | Q.S. | Q.S. | Q.S. | Q.S. | Q.S. |
| Water | Purified Water, USP | 100 | Q.S. to 100% | Q.S. to 100% | Q.S. to 100% | Q.S. to 100% | Q.S. to 100% |

*Activity in water. The aqueous phase may also contain some amounts of sodium chloride and impurities, such as fatty acid, fatty alcohol or fatty amine Tables 1a and 1b as well as Table 4 list polymers along with other formulation ingredients used for Inventive and Comparative Example Compositions. The following compositions, Inventive Examples (E1-E5) and Comparative Examples (C1-C12) were prepared utilizing different types of formulation ingredients (i.e. raw materials from various suppliers). These materials, along with INCI names, trade names and suppliers are listed below:

Zwitterionic Surfactants:
Cocamidopropyl Hydroxysultaine was obtained from Solvay Inc. as Mirataine™ CBS.
Cocamidopropyl Betaine was obtained from Evonik Inc. as TEGObetaine® L7-V Anionic surfactants:
Sodium C14-16 Olefin Sulfonate was obtained from Solvay Inc. as Rhodacal 246 FF.
Sodium C14-16 Olefin Sulfonate was obtained from Stepan as BioTerge® AS-40.
Sodium Hydrolyzed Potato Starch Dodecenylsuccinate was obtained from Akzo Nobel Personal Care as Structure™ PS-111.

Chelating Agents:
Tetrasodium EDTA was obtained from Dow Chemical as Versene™ 100XL.

Organic Acids/Preservatives:
Salicylic Acid was obtained from Rhodia as Salicylic acid PHA.
Sodium Benzoate, NF, FCC was obtained from Emerald Performance Materials.
Citric Acid was obtained from *Formosa* Laboratories Inc (for DSM) (Taiwan).

Humectants:
Sorbitol was obtained from the Archer Daniels Midland Company as Sorbitol USP/FCC.
Glycerin was obtained from Procter & Gamble Co. as Moon Glycerin USP/FCC.

Bases:

Sodium Hydroxide was obtained from EKA Chemicals as Sodium Hydroxide Pellets NF, FCC.

Preparation and Measurement of all Compositions of the Invention and Comparative Compositions All Inventive Compositions, E1-E5 and Comparative Examples C1-C12, were made in accordance with the following procedure: Unless otherwise indicated, all materials were added in amounts such that the compositions contain resulting weight percent amounts of active as indicated for each composition in Tables 1a and 1b. For example, 0.9% w/w active of Acrylates Copolymer (as given in table 1a, E1) corresponds to 3.0% w/w Aculyn Excel, which has an activity of 30% w/w; 0.9% w/w/30% w/w*100%=3.0% w/w.

Compositions E1-E5 and Comparative Examples C1-C8 were made as follows: To an appropriately sized vessel equipped with a hotplate and an overhead mechanical stirrer, the required amount of DI Water (Millipore, Model Direct Q), Sorbitol, Glycerin and polymer (for all compositions except C6 and C8) was added and mixed at 200-350 rpm until the mixture was homogeneous. Then, Sodium Hydrolyzed Potato Starch Dodecenylsuccinate (for all compositions except C6 and C7) was added and mixed until the mixture was homogeneous. Next, Sodium C14-16 Olefin Sulfonate and Sodium Hydroxide solution (20%) were added and the batch was heated to 50° C. under mixing and mixed at 200-350 rpm for 20 minutes. Then, Salicylic Acid (or Sodium Benzoate in case of E5) and EDTA were added and the batch was mixed until the mixture was homogenous. Then, Citric Acid (20% w/w solution in DI water) was added at room temperature to adjust to the desired pH value 4.0-4.5. Lastly, Cocamidopropyl Hydroxylsultaine was added. Water was added in q.s. to 100 wt %, and the batch was allowed to mix until uniform before being discharged to an appropriate storage vessel. Tables 1a, 1b list such compositions.

Comparative Examples C9-C12 were made as follows: To an appropriately sized vessel equipped with a hotplate and an overhead mechanical stirrer, the required amount of DI Water (Millipore, Model Direct Q), Glycerin and Sodium Hydrolyzed Potato Starch Dodecenylsuccinate was added and mixed at 200-350 rpm until the mixture was homogeneous. Then, Acrylates Copolymer was added and mixed until the mixture was homogeneous. Next, Alpha Olefin Sulfonate (only in case of C11-C12) and Sodium Hydroxide solution (20%) were added and the batch was heated to 50° C. under mixing and mixed at 200-350 rpm for 20 minutes. Then, EDTA and DMDM were added and the batch was mixed until the mixture was homogenous. Then, Citric Acid (20% w/w solution in DI water) was added at room temperature to adjust to the desired pH value 7.0-7.5 for C9 and C12; and to pH value 4.0-4.5 for C10 and C12. Lastly, Cocamidopropyl Betaine was added. Water was added in q.s. to 100 wt %, and the batch was allowed to mix until uniform before being discharged to an appropriate storage vessel. Table 4 lists such compositions.

TABLE 2

| Example | Clarity, NTU | Yield value, Pa | Brookfield viscosity, cps |
|---|---|---|---|
| E1 | 94 | 2.6 | 35,600 |
| E2 | 42 | 8.3 | 54,000 |
| E3 | 89 | 15.1 | 37,000 |
| E4 | 35 | 5.7 | 56,400 |
| E5 | 45 | 4.9 | 78,000 |
| C1 | 7 | 0 (no yield) | 110,000 |
| C2 | 14 | 0 (no yield) | 156,000 |
| C3 | 624 | 0 (no yield) | 8,160 |
| C4 | 106 | 2.2 | 11,040 |

TABLE 2-continued

| Example | Clarity, NTU | Yield value, Pa | Brookfield viscosity, cps |
|---|---|---|---|
| C5 | 149 | 0 (no yield) | 14,800 |
| C6 | 15 | 0 (no yield) | 44,800 |
| C7 | 107 | 4.6 | 45,360 |
| C8 | 17 | 0 (no yield) | 48,120 |

The Clarity, Yield values and Brookfield viscosities were measured in accord with the Clarity Test, Yield Values Test and Brookfield Viscosity Test, respectively, as described herein.

The results are shown in Table 2. As a result, applicants discovered that:

Compositions E1-E5, containing Acrylates Copolymer, or Acrylates Crosspolymer-4 or Structure® PLUS have exceptional clarity <95 NTU. Moreover, Acrylates Copolymer, Acrylates Crosspolymer-4 and Structure® PLUS have the tendency to build yield in compositions containing Sodium Hydrolyzed Potato Starch Dodecenylsuccinate, zwitterionic and anionic surfactants, and several other formulation ingredients;

Compositions C1-C2, with Carbomer and Acrylates/C10-30 Alkyl Acrylate Crosspolymer, have superior clarity but no yield. Increasing polymer concentration would results in unusable viscosity values as the Brookfield viscosities of C1 and C2 are already >100,000 cps;

Compositions C3-05 and C7 are not clear (>95 NTU);

Compositions C6 and C8 does not contain polymer and therefore do not have any yield.

Cell viability and IL-1α concentration were measured in accordance with EpiDerm™ Test as described herein. The results are shown in the Table 3. As a result, applicant discovered that Inventive compositions E2, E4 and E5 are mild formulas and exhibit cell viability of 99% and above with IL-1α concentration of 135-335 pg/mL.

TABLE 3

| Example | Clarity, NTU | Yield value, Pa | Cell viability, EIT, % | IL-1α, pg/mL |
|---|---|---|---|---|
| E2 | 42 | 8.3 | 103 | 278 |
| E4 | 35 | 5.7 | 99 | 335 |
| E5 | 45 | 4.9 | 99 | 135 |

Table 4 shows comparative example C9 from the prior art (U.S. Pat. No. 8,258,250 B2). The composition from this reference comprises a zwitterionic surfactant, Sodium Hydrolyzed Potato Starch Dodecenylsuccinate, an organic acid, and an Acrylates Copolymer as a suspending polymer. In comparison to this invention, C9 does not contain an anionic surfactant. The composition is stable and exhibits clarity (NTU=77) and a yield value of 2.0 Pa at a pH of >7 (specifically 7.2). Comparative example C10 shows the same formulation, but with a reduced pH compared to C9. Upon reducing the pH to a value covered in current invention (<7), the formula of the comparative example C10 is turbid (NTU>>100, specifically 1640 NTU at pH 4.3; the clarity deteriorates very obviously at pH values around 6.3) and phase separation is observed at room temperature (RT, 22° C.) within 24 hours. In addition, a Comparative Example C11 was made similar to C9 but with addition of anionic surfactant (Sodium C14-16 Olefin Sulfonate). Such composition (C11) exhibits clarity of 11 NTU and a yield value of 2.04 Pa at 7.2 pH value. However, reducing pH to pH 4.2 resulted in hazy formula (Comparative Example C12, 460 NTU) and the formula phase separates at RT within 24 hours.

TABLE 4

| Material, INCI | Trade Name | Activity (%) | C9 wt. % | C10 wt. % | C11 wt. % | C12 wt. % |
|---|---|---|---|---|---|---|
| Sodium Hydrolyzed Potato Starch Dodecenylsuccinate | NATRASURF ™ PS-111 | 100 | 9.18 | 9.18 | 9.18 | 9.18 |
| Acrylates Copolymer | Carbopol ® Aqua SF-1 | 30 | 2.1 | 2.1 | 2.1 | 2.1 |
| Cocamidopropyl Betaine | TEGObetaine ® L7-V | 30* | 2.1 | 2.1 | 2.1 | 2.1 |
| Sodium C14-16 Olefin Sulfonate | BioTerge ® AS-40 | 40* | 0 | 0 | 2.1 | 2.1 |
| Citric Acid solution | Citric Acid | 20 | Q.S. to pH 7.2 | Q.S. to pH 4.3 | Q.S. to pH 7.2 | Q.S. to pH 4.2 |
| Tetrasodium EDTA | Versene NA | 100 | 0.50 | 0.50 | 0.50 | 0.50 |
| Glycerin | Glycerin | 100 | 5.00 | 5.00 | 5.00 | 5.00 |
| DMDM | Glydant | 100 | 2.00 | 2.00 | 2.00 | 2.00 |
| Sodium Hydroxide solution (20%) | Sodium Hydroxide | 20 | Q.S. | Q.S. | Q.S. | Q.S. |

We claim:

1. A composition, comprising:
   an anionic surfactant,
   a zwitterionic surfactant,
   a superhydrophilic amphiphilic copolymer,
   an organic acid; and
   a non-crosslinked hydrophobically modified acid-swellable emulsion polymer,
   wherein said non-crosslinked hydrophobically modified acid-swellable emulsion polymer is present in an amount of about 0.1% to 5% by weight, and
   wherein said composition has an NTU value of 95 or less, a yield value of about 0.1 Pascal or more and a pH of from about 3 to about 6.5.

2. The composition of claim 1 comprising from about 0.5% to about 2.5% by weight of said non-crosslinked hydrophobically modified acid-swellable emulsion polymer.

3. The composition of claim 1 comprising from about 0.75% to about 2% by weight of said non-crosslinked hydrophobically modified acid-swellable emulsion polymer.

4. The composition of claim 1 having an NTU of about 75 or less.

5. The composition of claim 1 having a yield stress of 1 Pa or more.

6. The composition of claim 1 having a pH of from about 3 to about 5.5.

7. The composition of claim 1 comprising from about 1% to 25% by weight of said anionic surfactant.

8. The composition of claim 1 comprising from about 1% to about 25% by weight of said zwitterionic surfactant.

9. The composition of claim 1 comprising from about 0.1% to about 30% by weight of active of said superhydrophilic amphiphilic copolymer.

10. The composition of claim 1 comprising from about 0.05% to about 3.5% by weight of said organic acid.

* * * * *